(12) United States Patent
Shrivastava

(10) Patent No.: US 10,580,327 B1
(45) Date of Patent: Mar. 3, 2020

(54) HERNIA MODEL AND SURGICAL TRAINING SYSTEM

(71) Applicant: Shifali Shrivastava, Las Vegas, NV (US)

(72) Inventor: Shifali Shrivastava, Las Vegas, NV (US)

( * ) Notice: Subject to any disclaimer, the term of this patent is extended or adjusted under 35 U.S.C. 154(b) by 259 days.

(21) Appl. No.: 15/828,412

(22) Filed: Nov. 30, 2017

Related U.S. Application Data

(60) Provisional application No. 62/428,528, filed on Nov. 30, 2016, provisional application No. 62/429,067, filed on Dec. 1, 2016, provisional application No. 62/429,728, filed on Dec. 2, 2016, provisional application No. 62/431,418, filed on Dec. 7, 2016, provisional application No. 62/435,074, filed on Dec. 15, 2016, provisional application No. 62/441,334, filed on Dec. 31, 2016.

(51) Int. Cl.
*G09B 23/30* (2006.01)
*G09B 23/34* (2006.01)
*A61F 2/00* (2006.01)
*G09B 23/32* (2006.01)

(52) U.S. Cl.
CPC ........... *G09B 23/34* (2013.01); *A61F 2/0063* (2013.01); *G09B 23/32* (2013.01)

(58) Field of Classification Search
CPC ...... G09B 23/28; G09B 23/285; G09B 23/30; G09B 23/34
USPC ................................. 434/262, 267, 268, 272
See application file for complete search history.

(56) References Cited

U.S. PATENT DOCUMENTS

| | | | | |
|---|---|---|---|---|
| 5,518,406 A | * | 5/1996 | Waters | G09B 23/285 434/267 |
| 5,908,302 A | * | 6/1999 | Goldfarb | G09B 23/285 40/446 |
| 6,780,016 B1 | * | 8/2004 | Toly | G09B 23/285 434/262 |
| 8,297,982 B2 | * | 10/2012 | Park | G09B 23/34 434/262 |

(Continued)

OTHER PUBLICATIONS

Coddington, Carmen et al., Inguinal Hernia Model, Final Poster, May 6, 2010, University of Wisconsin, Madison Wisconsin.

(Continued)

*Primary Examiner* — Kurt Fernstrom
(74) *Attorney, Agent, or Firm* — Gentry McLean, PLLC

(57) ABSTRACT

An embodiment of a system for anatomical training includes a portable base unit, a flexible simulated abdominal wall module, a flexible simulated cutaneous module and a simulated hernia module. An embodiment of a method of assembling a system includes attaching a flexible simulated abdominal wall module to a portable base unit, attaching a flexible simulated cutaneous module to one or more of the simulated abdominal wall module or the portable base unit, and positioning a simulated hernia to be extended through an opening in the simulated abdominal wall module. An embodiment of a method of using a system includes forming an opening in a flexible simulated cutaneous module, locating a simulated hernia extending through an opening in an underlying simulated abdominal wall module, performing a repair of the simulated hernia, and closing the opening in the simulated cutaneous module.

23 Claims, 15 Drawing Sheets

(56) References Cited

U.S. PATENT DOCUMENTS

| | | | | |
|---|---|---|---|---|
| 10,140,889 B2* | 11/2018 | Black | ................... | G09B 23/30 |
| 10,198,966 B2* | 2/2019 | Wachli | ................ | G09B 23/285 |
| 10,380,922 B2* | 8/2019 | Belzacq | ................... | G09B 9/00 |
| 2012/0148994 A1* | 6/2012 | Hori | ..................... | G09B 23/30 |
| | | | | 434/272 |
| 2014/0272878 A1* | 9/2014 | Shim | ..................... | G09B 23/30 |
| | | | | 434/272 |
| 2014/0329217 A1* | 11/2014 | Barsness | ............. | G09B 23/306 |
| | | | | 434/272 |
| 2015/0031008 A1* | 1/2015 | Black | ................. | G09B 23/285 |
| | | | | 434/272 |

OTHER PUBLICATIONS

Coddington, Carmen et al., Inguinal Hernia Model, Final Project Report, Apr. 30, 2010, University of Wisconsin, Madison Wisconsin.
Coddington, Carmen et al., Inguinal Hernia Model, Project Report, Mar. 9, 2010, University of Wisconsin, Madison, Wisconsin.
Mayo Clinic, Stitch by Stitch—Mayo Clinic Hernia Repair Model Helps Surgeons Hone Critical Skills, Sharing Mayo Clinic, Aug. 23, 2017, available at https://sharing.mayoclinic.org/2017/08/23/stitch-by-stitch-mayo-clinic-hernia-repair-model-helps-surgeons-hone-critical-skills/.
Simulab Corporation, Hernia Model, 2015 Product Catalog, 2015, p. 34, Simulab Corporation, Seattle WA.

* cited by examiner

HERNIA MODEL AND SURGICAL TRAINING SYSTEM

RELATED APPLICATIONS

This application claims the benefit of the following U.S. Provisional Applications, each entitled "Training Model for Hernia Anatomy": App. No. 62/428,528 filed on Nov. 30, 2016; App. No. 62/429,067 filed on Dec. 1, 2016; App. No. 62/429,728 filed on Dec. 2, 2016; App. No. 62/431,418 filed on Dec. 7, 2016; App. No. 62/435,074 filed on Dec. 15, 2016; and App. No. 62/441,334 filed on Dec. 31, 2016. Each of these provisional applications is hereby incorporated by reference in its entirety and for all purposes, as if completely set forth herein.

BACKGROUND

Hernia and abdominal wall anatomy is confusing for new medical students and residents. The spatial concepts of the area can best be understood by using a model that can be manipulated several times until the concept is clear. A model of the relevant anatomy can help in developing psychomotor skills and could also serve as a tool to communicate with patients.

For surgical training in particular, a model providing for cutting and/or suturing practice is desirable. Similarly, a mechanism to represent the actual hernia of different types is also desirable to facilitate visual, spatial and tactile learning. Cost-effective replacement of cut portions is desirable as well, so that repeated use can be accommodated, particularly in medical school or residency environments. Currently-available hernia anatomy models have high purchase and part replacement costs, and often do not provide a realistic tactile experience during surgery simulation.

BRIEF DESCRIPTION OF THE DRAWINGS

The following detailed description of various disclosed embodiments makes reference to the accompanying drawings in which.

DETAILED DESCRIPTION

Embodiments of the training models described herein provide for low-cost, realistic surgical training. Embodiments of the training models are also designed to provide realistic anatomical dimensions while having an overall size that is more portable than some existing models.

Ventral Hernia Training Model

In general, a hernia is a protrusion of an organ or other bodily structure through the wall that normally contains it. An abdominal hernia is a hernia located at a defect in the abdominal wall, where the abdominal wall includes multiple layers of muscle, fat and connective tissue. A ventral hernia occurs on the ventral, or front, side of the patient's abdomen. An embodiment of the ventral training model described herein simulates a hernia involving a portion of the abdominal wall containing the rectus abdominis muscles or associated connective tissue. Such a hernia is in some embodiments an incisional hernia, in which a portion of the intestine or some other tissue protrudes through a weakened portion of the abdominal wall associated with a previous incision and/or thinning of old scar tissue.

One or more embodiments of a training model for open ventral hernia reduction procedures are described herein with reference to the drawings filed herewith. Component parts of embodiments of a ventral hernia training model are illustrated by FIGS. 1A-5D.

Base Unit

Figure 1A:
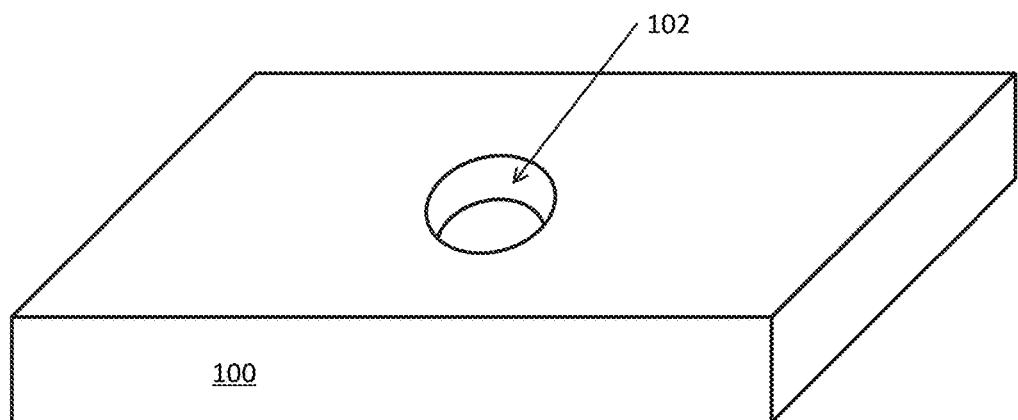
FIG. 1A is a diagram illustrating certain aspects of an embodiment of a base unit for a ventral hernia anatomy training model as described herein.

FIG. 1A is a simplified diagram illustrating certain aspects of a base unit 100 for a hernia training model. The base unit includes a cavity 102, which represents the abdominal cavity or a portion thereof, within its upper surface suitable for housing a simulated hernia. Suitable cavity dimensions may vary depending on the size of hernia involved. In an embodiment, the cavity dimensions are determined by a user of the training model in view of the size and type of hernia to be simulated. The cavity may be significantly larger than the simulated hernia in some embodiments, which may allow for user-end adaptability to represent various types and sizes of hernias.

In an embodiment, the cavity has a diameter of between approximately two inches and approximately four inches, and a depth of between approximately one inch and approximately three inches. In an embodiment, the cavity opening has a circular or elliptical shape. In other embodiments, the cavity opening can be rectangular or have any other shape allowing a simulated hernia to be pushed into or pulled out of the cavity from above. According to ventral hernia type (epigastric, incisional, umbilical), the cavity opening may be rectangular to better represent a defect in the rectus abdominis muscle and/or abdominal wall layer(s). Allowing a simulated hernia to be pushed into or pulled out of the cavity can be used in demonstrating a patient pushing their abdomen out and causing the hernia to bulge. This allows the concept of a reducible (may be pushed back into the abdominal cavity) or non-reducible hernia to be illustrated. Furthermore, it allows the mechanical skill of correcting and managing the hernia when opening the abdominal wall layers and then correcting the fascial defect. Although cavity 102 is positioned approximately at the center of the upper surface of base unit 100, the cavity is not necessarily centered in other embodiments, as different hernia types and locations may be represented accordingly by providing unique simulated fascial layers and anatomical representation. In some embodiments, a base unit may include more than one cavity. Such an embodiment could be useful in various situations, such as for training sessions with multiple hernias, or for allowing a choice between training with different types of hernias.

In an embodiment, an outer perimeter of the base unit has a substantially rectangular shape when viewed from above, representing a patient's torso. In a further embodiment, an area subtended by the base unit approximates an area of a patient's skin exposed by a patient drape used during surgery. The base unit may have other shapes or sizes in different embodiments, however. In an embodiment, the base unit is dimensioned to be readily carried by a person—i.e., portable. For example, the length and width of the base unit, when viewed from above, are each in a range between approximately six inches and approximately eighteen inches in one such embodiment. In a further embodiment, the length and width are each in a range between approximately eight inches and approximately fifteen inches. A height of the base unit, when viewed from the side, ranges in one embodiment from approximately one inch to approximately six inches. In a further embodiment, the height is in a range between approximately two inches and approximately four inches. The base unit may be formed from any material or combination of materials allowing for formation of the cavity, and providing sufficient support for overlying layers of the training model. The base unit may also include a fixation or gripping mechanism (including, but not limited to, non-surface-damaging adhesive or small suction cups) on its lower surface to allow temporary fixation to a table top or other smooth surface for added stability. In an embodiment, an upper surface of the base unit surrounding the cavity opening is configured to simulate an outer surface of the peritoneal layer of the abdominal wall. For example, the upper surface of the base unit is in some embodiments rendered in a red or pink color. In a further embodiment, the upper surface of the base unit surrounding the cavity opening is configured to exhibit a partial compressibility, which may simulate flexibility associated with the peritoneal layer or other abdominal wall layer.

In another embodiment, the upper surface of the base unit is formed from or coated with a water-resistant material. Such an embodiment may allow use of the base unit in training sessions in which liquids or gels are added to overlying layers. Addition of liquids or gels may be done to simulate body fluids and/or fluids added during a procedure, such as blood or BETADINE® sterilization solution. Such an embodiment may provide the added psycho-mechanical practice of an open inguinal hernia repair procedure starting from the preparation of surgical site and including handling of mesh placement and suturing under more realistic conditions.

One or more removable fastener elements may be attached to the upper surface of the base unit in some embodiments. Such fastener elements may allow removable connection to overlying layers of a ventral hernia training model. This removability may assist instructors or users in evaluating quality of suture placement technique on the simulated fascial layers. It may also provide for efficient replacement of overlying layers for repeated practice. In an embodiment, a removable fastener element attached to the base unit includes one side of a snap fastener, or one side of a hook-and-loop fastener such as VELCRO®. Although illustrated as a monolithic unit in the simplified diagram of FIG. 1A, the base unit is in an embodiment formed from a combination of elements and/or layers. In such an embodiment, the constituent elements of layers of the base unit may be made from different materials or combinations of materials.

Figure 1B:
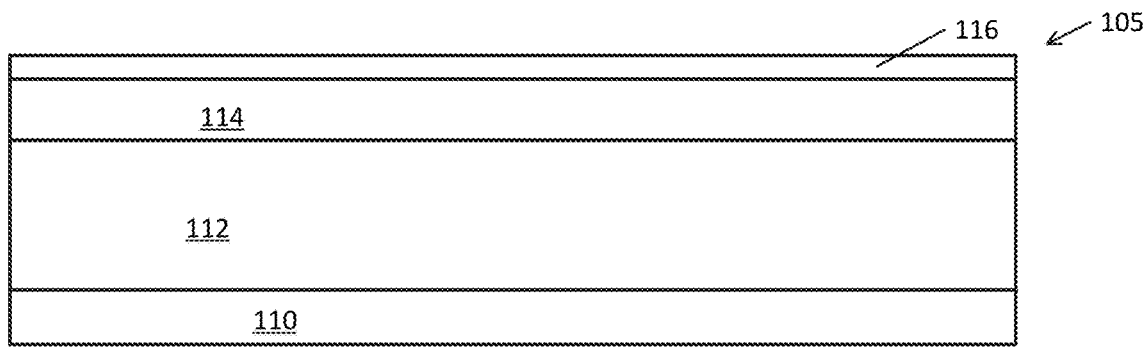
FIG. 1B is a cross-sectional diagram illustrating certain aspects of an embodiment of a base unit for a ventral hernia anatomy training model.

A cross-sectional view of a multilayered embodiment of a base unit is shown in FIG. 1B. The view of FIG. 1B is oriented such that the left side of the cross-section of FIG. 1B could correspond to the front face, and the right side to the left face, of a base unit shown in a perspective view such as FIG. 1A. The cross-section of FIG. 1B is taken through a portion of the base unit not including the cavity for the simulated hernia. Base unit 105 in FIG. 1B includes a rigid base layer 110, a substantially incompressible layer 112, a partially compressible layer 114 and a flexible cover layer 116. Rigid base layer 110 is made from a rigid material such as wood, rigid plastic, metal, rigid cardboard, an extruded polystyrene such as STYROFOAM®, any other material suitable for a rigid base layer, or any combination of such materials. In an embodiment, rigid base layer 110 is made from one or more materials with sufficient mass that the base unit can be expected to remain stationary during training sessions. Alternatively or in addition, rigid base layer 110 may include a mechanism for temporary fixation to an underlying surface, such as suction cups or removable, non-surface-damaging adhesives. In a further embodiment, rigid base layer 110 is made from a precut wooden element such as a wooden plaque.

Substantially incompressible layer 112 of base unit 105, in an embodiment, provides height to accommodate the formation of the cavity within the base unit and is formed from a material allowing formation of the cavity. In an embodiment, layer 112 is substantially incompressible, in the sense that the thickness of layer 112 remains substantially fixed during normal use of the training model. Layer 112 can be made from rigid materials similar to those described for rigid base layer 112. In an embodiment, layer 112 comprises a rigid foam layer, such as extruded polystyrene or expanded polystyrene. In a further embodiment, layer 112 comprises multiple stacked layers. For example, layer 112 may be formed from multiple layers of laminated foam board having a foam core between smooth outer layers of paper, cardboard, or plastic. Partially compressible layer 114, in an embodiment, provides a partial compressibility from above for an upper surface of the base unit, which may help to more realistically simulate a bodily structure. Layer 114 may be made from a partially compressible material such as a flexible foam, flexible sponge material, fiber batting, a flexible gel-filled structure, or other material providing some degree of compressibility. In an embodiment, layer 114 is formed from a material suitable for having a portion removed to form part of the cavity within the base unit. In another embodiment, layer 114 is formed from a material that may be shaped to fit around the cavity.

Flexible cover layer 116 of base unit 105 is formed from a flexible material such as cloth, mesh, flexible plastic sheet or film, flexible foam sheet, natural or simulated leather, or other flexible material. In an embodiment, layer 116 has an extended area and is wrapped around to cover the lateral surfaces of base unit 105, and affixed to rigid base layer 112. In a further embodiment, layer 116 is wrapped around the sides of base unit 105 and affixed to a lower surface of rigid base layer 112. In an embodiment, layer 116 may be affixed to base layer 112, or another portion of base unit 105, using a relatively permanent method such as glue, staples, or tacks. Alternatively, layer 116 may be affixed to base layer 112 or another portion of base unit 105 using a releasable method such as snaps or hook and loop fasteners. In an embodiment, layer 116 is attached such that it remains intact during model use, yet also allows for relatively easy replacement of base unit parts if needed. Such replacement may be performed, for example, in the event of damage of a foam layer through the use of fluids or gels. In an embodiment, layer 116 has a color suitable for simulation of an outer peritoneal layer. In a further embodiment layer 116 has a red or pink color. One or more removable fastener elements may be attached to an upper surface of layer 116 in some embodiments. Such fastener elements may allow removable connection to overlying layers of a ventral hernia training model. In an embodiment, a removable fastener element attached to layer 116 includes one side of a snap fastener, or one side of a hook-and-loop fastener such as VELCRO®. Any other suitable fasteners may be used in other embodiments, including but not limited to tapes or other adhesives.

Figure 1C:
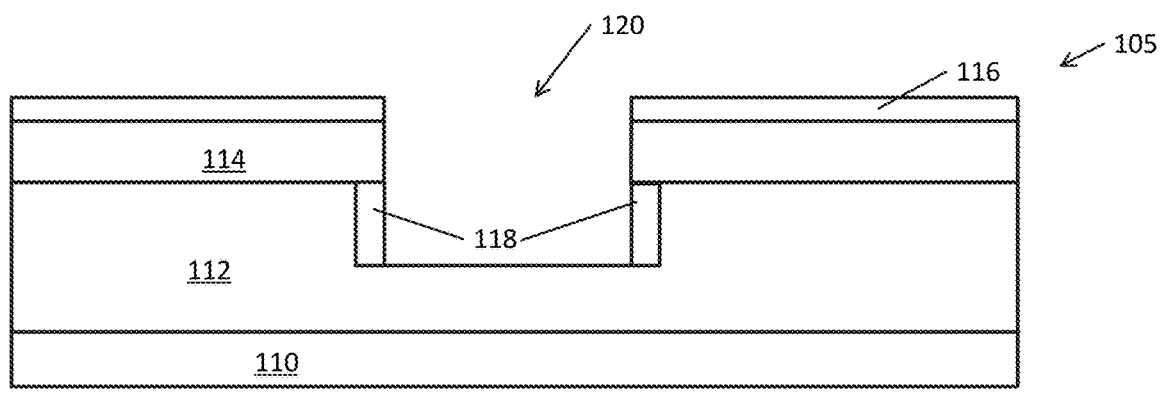
FIG. 1C is a cross-sectional diagram illustrating certain aspects of an embodiment of a base unit for a ventral hernia anatomy training model.

A different cross-sectional view of base unit embodiment 105 is shown in FIG. 1C. The view of FIG. 1C is a cross-section of a cut passing through the cavity of base unit 105. Cavity 120 of base unit 105 is similar to cavity 102 of base unit 100, discussed further above in connection with FIG. 1A. In the embodiment of FIG. 1C, base unit 105 further includes a cylindrical wall element 118 forming a portion of the wall of cavity 120. In an embodiment, wall element 118 is a cylindrical foam structure. In a further embodiment, wall element 118 is cut from premanufactured cylindrical foam material such as pipe insulation stock or a beverage can insulator. Such a premanufactured material can provide a smooth layer to represent the abdominal fascia and defect, especially if used in combination with a gel or liquid simulating body fluids. In the embodiment of FIG. 1B, wall element 118 is situated within the portion of cavity 120 formed within layer 112, and overlying layers 114 and 116 extend over wall element 118. In other embodiments, a wall element such as wall element 118 may extend along a different portion of the cavity wall, or along the entirety of the cavity wall. In still further embodiments, the cavity does not include a wall element such as wall element 118.

In an embodiment of base unit 105, a portion of cover layer 116 extends into cavity 120. Cover layer 116 is formed from a material resistant to water or other liquids in some embodiments. In further embodiments, other layers of base unit 105 are formed from liquid-resistant materials. Base unit 105 of FIGS. 1B and 1C is merely an exemplary embodiment, and base units such as base unit 100 of FIG. 1A are not limited to the specific form of base unit 105.

Hernia Model Assembly

An example of a hernia model assembly for use with the base unit described above is illustrated in FIGS. 2A-3B. In the embodiment shown in a simplified perspective view in FIG. 2A, hernia model assembly 200 includes a container 202 and hernia model 206. In this embodiment, container 202 includes an upper surface 204 having an opening through which hernia model 206 can extend.

In an embodiment, container 202 is dimensioned for placement into the cavity of a base unit such as those described in connection with FIGS. 1A through 1C above. Although shown in FIG. 2A as having a cylindrical shape, container 202 may have other shapes. For example, container 202 may have sloped rather than vertical sidewalls, or may have a "footprint" of rectangular or some other shape rather than circular. Container 202 can be formed from any material sufficiently rigid to allow it to maintain its shape during normal use of the training model. For example, in one embodiment a container 202 can be fashioned using a plastic cup to form the bottom and sides of the container.

Figure 2A:
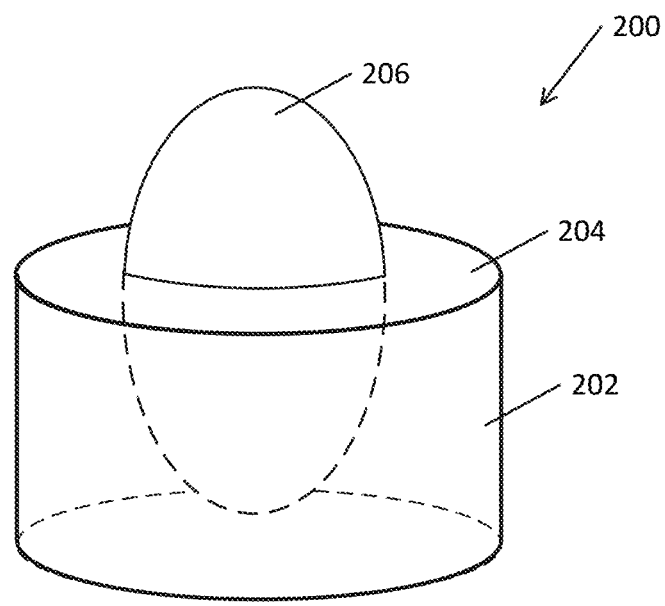
FIG. 2A is a diagram illustrating certain aspects of an embodiment of a hernia model assembly for a ventral hernia anatomy training model.

Upper surface 204 shown in FIG. 2A may in some embodiments be integral to container 202. In other embodiments, upper surface 204 is provided by a removable cap to container 202. A removable cap may be formed from any suitable material and attached by any suitable mechanism. For example, a cap formed from a relatively flexible material, such as rubber or certain plastics, may be attached using a snap-fit mechanism or a simple compression grip mechanism. Other mechanisms such as threaded caps could also be used with appropriate cap and container materials. An opening in upper surface 204 to allow protrusion of hernia model 206 may take any suitable form, such as a hole or one or more slits. In an embodiment, the opening is configured to provide a degree of friction or compression to the protruding hernia model to help hold the hernia model in place during use of the training model (until the hernia is pushed back into the cavity during simulation of hernia repair).

In a further embodiment, upper surface 204 may be formed from a very flexible material, such as sheet plastic or cloth. For example, upper surface 204 may in some embodiments be formed from plastic used in balloons or in gloves. In some embodiments employing a flexible upper surface material, the upper surface is held onto container 202 using a retaining ring positioned at the perimeter of the upper surface. Such a retaining ring could be formed, for example, from the outer portion of a cap dimensioned to fit onto container 202, where the central portion of the cap has been removed. In other embodiments, use of a flexible upper surface material having some degree of elasticity may allow the flexible material to "grip" the outer sidewalls of container 202 such that a retaining ring is not needed.

In some embodiments employing a flexible upper surface, or upper surface portion, the amount and shape of the flexible material is such that it can extend upward and form a covering for the hernia model when the hernia model is arranged to protrude from the cavity of the base unit. In such an embodiment, the flexible upper surface may simulate a hernia covering layer derived from one or more layers of the abdominal wall, such as a peritoneal layer. In a further embodiment, this covering layer is cut through, and possibly cut away, during a simulated hernia repair using the training model. In such an embodiment, additional flexible upper surface materials may be made available as replacement parts.

In one low-cost embodiment of a hernia model container, container 202 is formed using a small plastic cup such as those used by food service providers to package condiments or salad dressings. Upper surface 204 is formed in one such embodiment from a plastic lid used for covering such a food service cup. In another embodiment, the outer portion of such a plastic lid is used as a retaining ring for an upper surface formed from a flexible plastic material.

In some embodiments, upper surface 204 has a color similar to that of a base unit cover layer such as cover layer 116 of FIG. 1C. As such, upper surface 204 may in such an embodiment have a color suitable for simulation of an outer peritoneal layer. In a further embodiment, upper surface 204 may have a red or pink color.

Figure 2B:
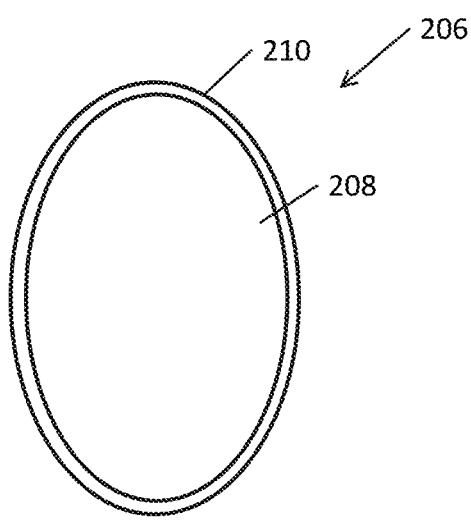
FIG. 2B is a cross-sectional diagram illustrating certain aspects of an embodiment of a hernia model for a ventral hernia anatomy training model.

Although shown as oval-shaped in FIGS. 2A and 2B for simplicity, hernia model 206 may have any suitable shape. Hernia model 206 is used to simulate a hernia during use of the hernia training model, and as such is capable of being positioned in a way that, when the hernia training model is set up for use, hernia model 206 extends from a cavity in a base unit such as those of FIGS. 1A-1C. During simulated hernia repair, hernia model 206 is then pushed back into the cavity of the base unit.

The simplified cross-sectional view of FIG. 2B illustrates main portions of an embodiment of hernia model 206. This embodiment of hernia model 206 includes a simulated hernia sac 210 surrounding a simulated hernia body, or contents, 208. In an embodiment, simulated hernia sac 210 is formed from a thin, flexible material such as plastic film or fabric. For example, simulated hernia sac 210 may be formed from a portion of a plastic bag or sleeve. In some embodiments of a simulated hernia repair process, simulated hernia sac 210 is cut through, and possibly cut away. In such an embodiment, additional simulated hernia sacs, or materials for forming same, may be made available as replacement parts. In certain embodiments, simulated hernia sac 210 may be combined with or incorporated into a flexible version of upper surface 204 as described above.

Simulated hernia contents 208 may have any suitable shape or appearance, as long as the hernia model can be extended from and pushed back into a cavity in the hernia training model. In an embodiment, for example, simulated hernia contents 208 may be shaped to simulate a portion of bowel and a portion of the intervening omentum. Simulated hernia contents 208 are in some embodiments formed from materials having a degree of malleability and/or compressibility, or combinations of such materials. For example, modeling clay, foam, or sponge may be used, as well as softer plastics or elastomers like silicones or silicone rubber, or gel-filled casings of flexible plastics. Other suitable materials may include, but are not limited to, fabrics, fibers, fiber-based balls or battings, strings or yarns. Colors of materials may be chosen to simulate colors of typical biological hernia contents. In some embodiments, a selection of hernia models 206 representing various sizes and specific hernia contents (e.g., bowel, bladder, etc.) is made available.

Figure 3A:
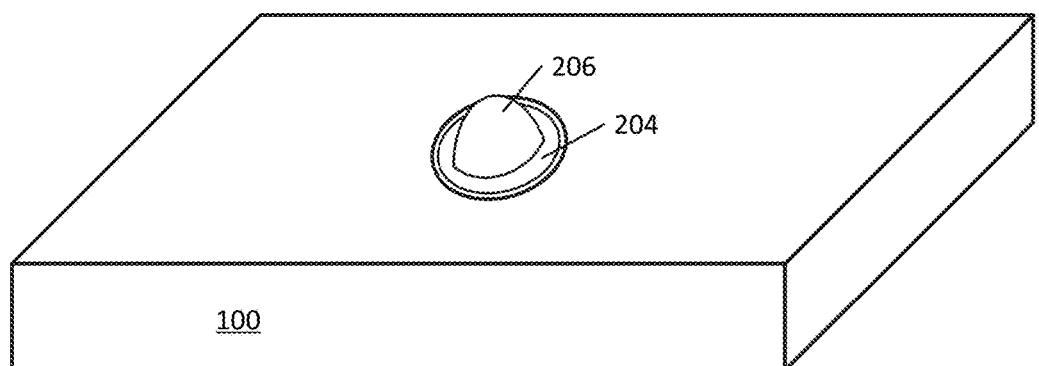
FIG. 3A is a diagram illustrating certain aspects of an embodiment of a base unit combined with an embodiment of a hernia model assembly.
Figure 3B:
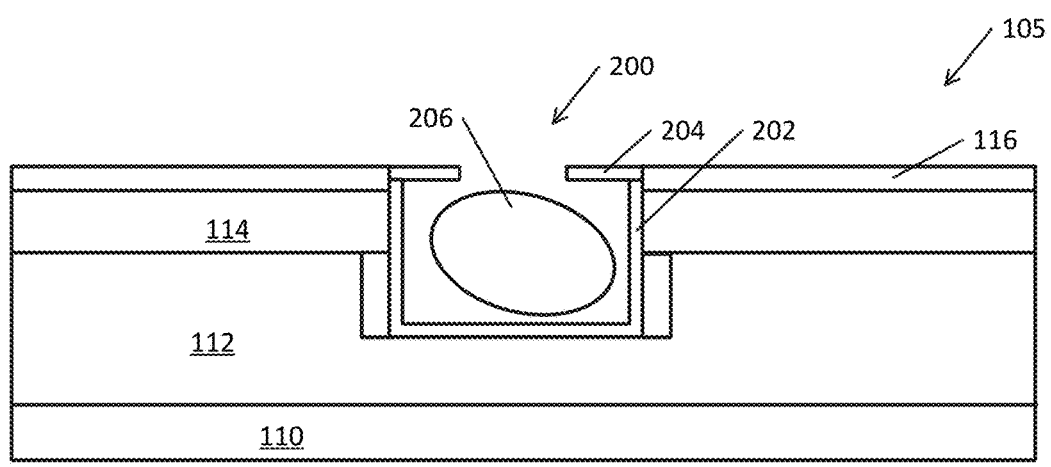
FIG. 3B is a cross-sectional diagram illustrating certain aspects of an embodiment of a base unit com combined with an embodiment of a hernia model assembly.

A simplified perspective view of a base unit having a hernia model assembly inserted into its cavity is shown in FIG. 3A. In the embodiment of FIG. 3A, hernia model 206 is positioned to extend upward from container 202 and the upper surface of base unit 100. This type of hernia model positioning is used when setting up a training model for a simulated hernia reduction procedure. A simplified cross-sectional view of a hernia model assembly inserted into a cavity of a multilayered embodiment of a base unit is shown in FIG. 3B. In the embodiment of FIG. 3B, hernia model 206 is fully contained within container 202, and therefore within the cavity of base unit 3B. This type of hernia model positioning results from "reduction" of the simulated hernia during use of the hernia training model, and may be used to make the hernia training model more flat and compact for storage or transport.

Although not explicitly shown in FIGS. 3A and 3B, some type of non-permanent fastener may be used, in some embodiments, between the hernia model assembly and the cavity of a base unit to help hold the hernia model assembly in the base unit. For example, adhesive tape or some other adhesive product may be used. Other examples include snap fasteners or hook-and-loop fasteners. In other embodiments, no fasteners are used to hold the hernia model assembly into the base unit. In some embodiments, the hernia model assembly is heavy enough to stay sufficiently fixed within the base unit during use of the hernia training model. In some embodiments, the shapes of the hernia container and cavity are such that the hernia model assembly is under some degree of compression when inserted into the base unit. In an embodiment, the hernia model assembly includes a small handle or other feature at or near its upper surface which facilitates insertion and removal of the hernia model assembly into and from the base unit cavity.

In some embodiments, the hernia model is attached in some way to the interior of a container of the hernia model assembly. For example, a fastener or adhesive may be used to attach a lower surface of the hernia model to the bottom interior surface of the container. In a further embodiment, the hernia model may be attached to the interior of the container using a spring mechanism, such that the spring is extended when the hernia model extends upwards out of the cavity, and the spring is compressed when the hernia model is pushed into the cavity. In a still further embodiment, such a spring mechanism may include a lock-down mechanism to keep the spring compressed after the hernia is pushed into a cavity. For example, such a lock-down mechanism may include a ring attached to the hernia model, and surrounding the spring, where the ring is configured to lock, upon rotation, into a retaining ring attached to the bottom interior surface of the container (and also surrounding the spring). In another embodiment, the hernia model is configured to allow it to be inflated by either manual or automatic means. In such an embodiment, inflation of the hernia model causes it to extend out of the cavity of the base unit.

Multiple variations and modifications of the embodiments described herein will be apparent to those of ordinary skill in the art in view of this disclosure. For example, in some embodiments a container in a hernia model assembly is an open container, without an upper surface such as upper surface 204. An upper surface or cap to the container may especially be unnecessary for embodiments in which the hernia model is attached to an interior surface of the container. As another example, container 202 may not be used in some embodiments, such that a hernia model, rather than an entire hernia model assembly, is placed into a cavity of a base unit. In an embodiment not using a container, the hernia model may be attached to an interior surface of the cavity in the base unit, by methods such as those described above for attaching the hernia model assembly to the cavity or for attaching the hernia model to the container.

Embodiments of the hernia model, container, and hernia model assembly can be supplied separately as complete assemblies, and can be supplied in combination with or separately from embodiments of the base unit and other training model components described herein.

Abdominal Wall Module

Figure 4A:
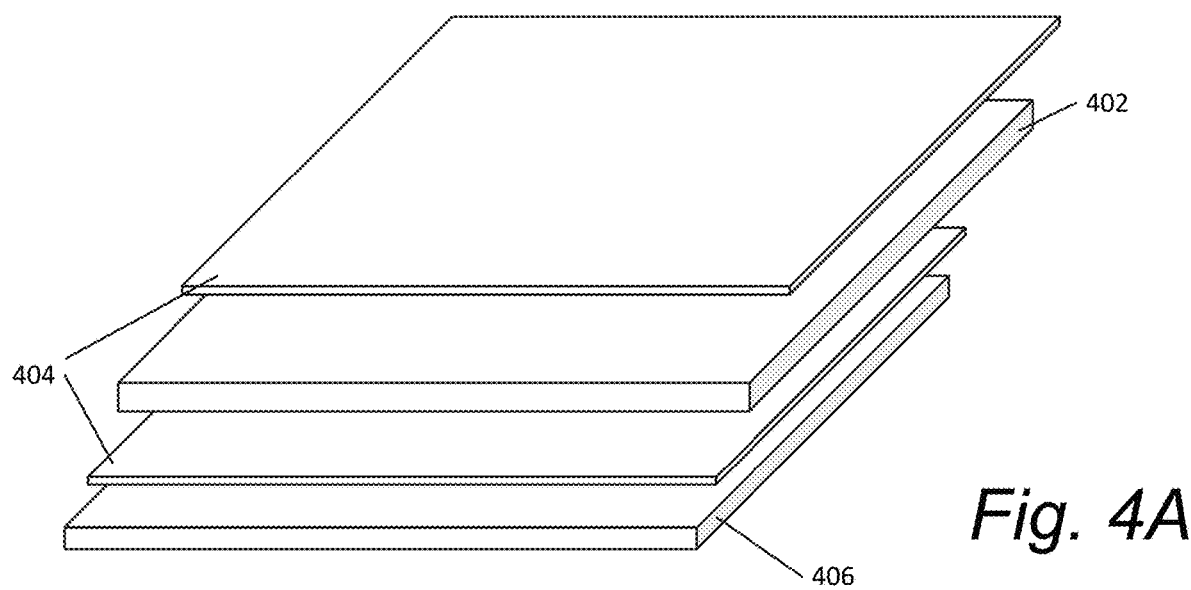
FIG. 4A is a diagram illustrating component layers of an embodiment of an abdominal wall module for a ventral hernia anatomy training model.
Figure 4B:
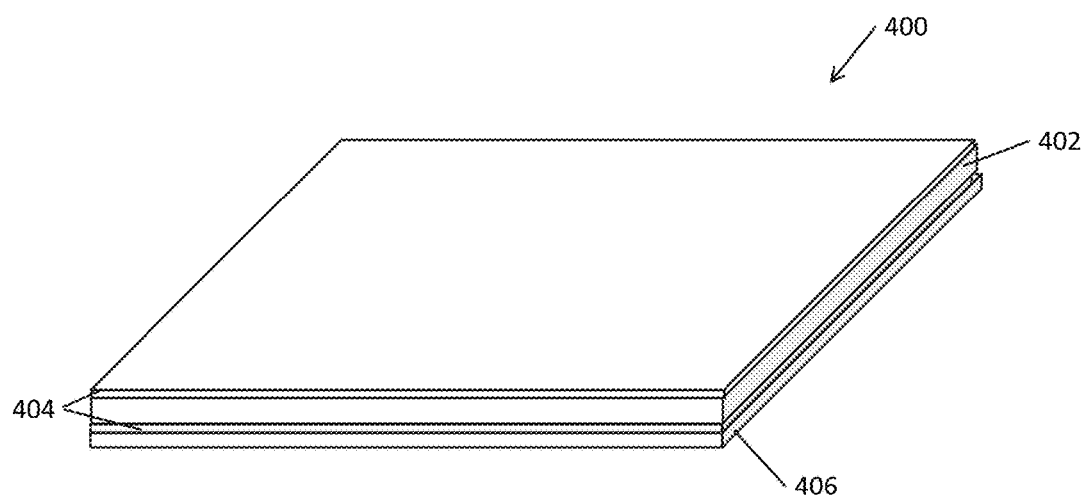
FIG. 4B is a diagram illustrating certain aspects of an embodiment of an abdominal wall module for a ventral hernia anatomy training model.

Perspective views of an embodiment of an abdominal wall module for a hernia training model are shown in FIGS. 4A and 4B. In this embodiment, abdominal wall module 400 has four component layers. The layers are separated for clarity in the exploded view of FIG. 4A, and shown attached to one another in the view of FIG. 4B. Layer 402 is a muscle simulation layer. In an embodiment, layer 402 simulates the rectus abdominis muscle. Layer 402 is formed from a flexible or supple material, such as, for example, a flexible foam sheet. In an embodiment, layer 402 has a thickness comparable to that of an abdominal muscle layer. In a further embodiment, layer 402 has a thickness between approximately one millimeter and approximately one centimeter. In an embodiment, layer 402 has a color similar to that of a muscle layer. In a further embodiment, layer 402 is formed from a red or reddish material.

Layers 404 on either side of muscle simulation layer 402 are fascia simulation layers, where fascia is a type of connective tissue. In an embodiment, fascia simulation layers 404 are formed from a thin, somewhat sheer material, including but not limited to a mesh-type material. Fascia simulation layers 404 are in some embodiments relatively thin compared to muscle simulation layer 402. In a further embodiment, fascia simulation layers 404 each have a thickness of approximately one millimeter or less. In an embodiment, layers 404 have a color similar to that of a fascia layer. In a further embodiment, layers 404 are formed from a white or similarly light-colored material.

Layer 406 is a fat simulation layer. In an embodiment, layer 406 simulates an extraperitoneal fat layer. In an embodiment, layer 406 is formed from a flexible or supple material, such as, for example, a flexible foam sheet. In an embodiment, layer 406 has a thickness comparable to that of a patient's extraperitoneal fat layer. In a further embodiment, layer 406 has a thickness of between approximately one millimeter and approximately one centimeter. In an embodiment, layer 406 has a color similar to that of a fat layer. In a further embodiment, layer 406 is formed from a yellow or yellowish material.

The component layers of abdominal wall module 400 are attached to one another to form a stack, as illustrated by FIG. 4B. In an embodiment, the layers are attached at one or more points at or near the lateral perimeter of module 400, and are not bonded together in the central part of the module. Such an embodiment allows for simulation practice of surgical dissection and retraction in the central part of the module, as performed in an open inguinal hernia repair procedure. In some embodiments, one or more of the layers are attached together in a removable fashion, such as by hook-and-loop fasteners or non-permanent adhesives. Such removable attachment may be useful in embodiments where adding spacer elements between layers is desired. Adding spacer elements between layers can be used to simulate expansion caused by insufflation during a surgical procedure, as discussed further below in connection with FIGS. 4D and 4E. In other embodiments, one or more of the layers are attached together in a more permanent fashion, such as stapling, stitching, and heat and/or compression bonding.

When configured for a simulated hernia repair operation using the ventral hernia training model, abdominal wall module 400, in an embodiment, includes an opening into which a hernia model such as hernia model 206 protrudes. In an embodiment, abdominal wall module 400 is supplied with an opening, such as a hole or slit, already formed. In an alternative embodiment, abdominal wall module 400 is supplied with its layers intact, so that an opening suitable for the specific configuration of the hernia training model can be formed when setting up the hernia training model for use. In some embodiments, abdominal wall module 400 is formed to have a locally smaller thickness of one or more of its constituent layers in the region of the simulated hernia defect. In another embodiment, one or more slits, or "incisions," of one or more layers within abdominal wall module 400 are made by the end user, harnessing tactile skill to practice sizing of incision in the surgical procedure using anatomical landmarks provided such as umbilicus (navel), pelvis, midline, etc.

Figure 4C:
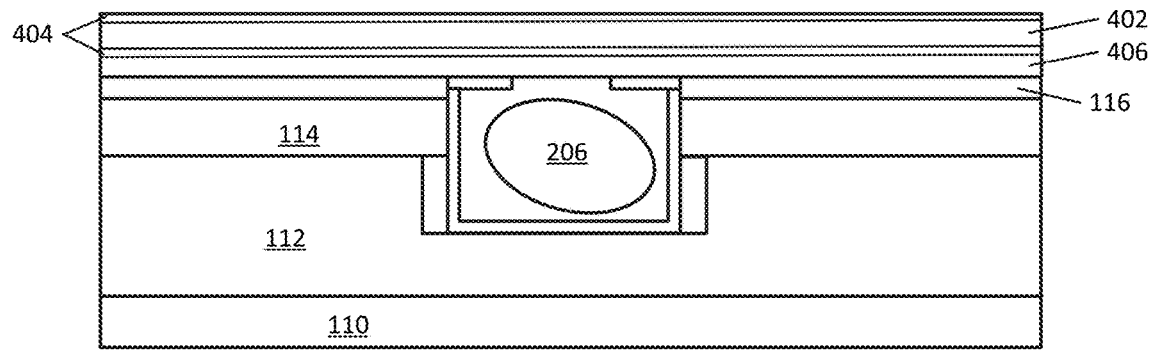
FIG. 4C is a cross-sectional diagram illustrating certain aspects of an embodiment of an abdominal wall module overlying an embodiment of a base unit combined with an embodiment of a hernia model assembly.

A simplified cross-sectional view of an abdominal wall module overlying a base unit and hernia model assembly is shown in FIG. 4C. It is noted that, in an embodiment, an opening (not shown) in the abdominal wall module is provided when the assembly of FIG. 4C is prepared for a simulated hernia repair. In an embodiment, the lower surface of the abdominal wall module is directly attached to the upper surface of the base unit. In a further embodiment, the abdominal wall module is attached to the base unit in a removable fashion, such as using snaps, hook-and-loop fasteners, tape, or non-permanent adhesive.

Figure 4D:
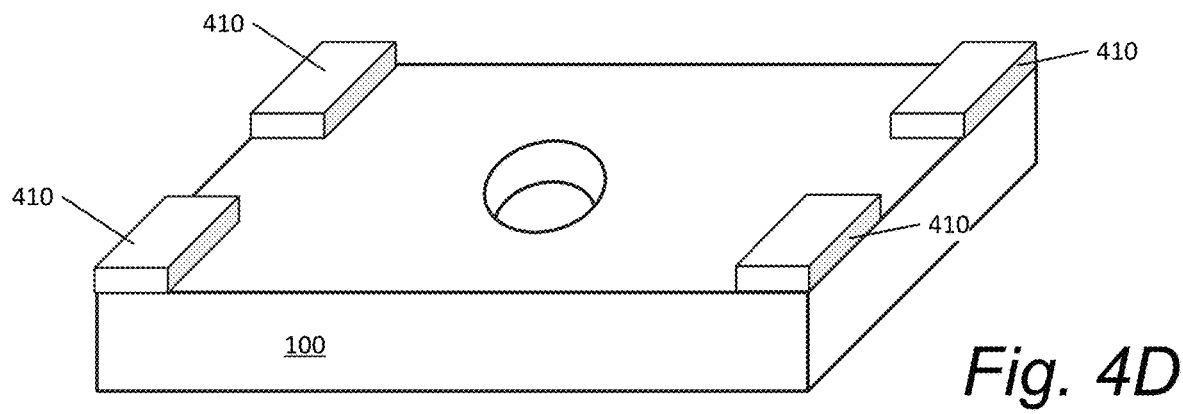
FIG. 4D is a diagram illustrating certain aspects of an embodiment of a base unit with overlying spacer elements.
Figure 4E:
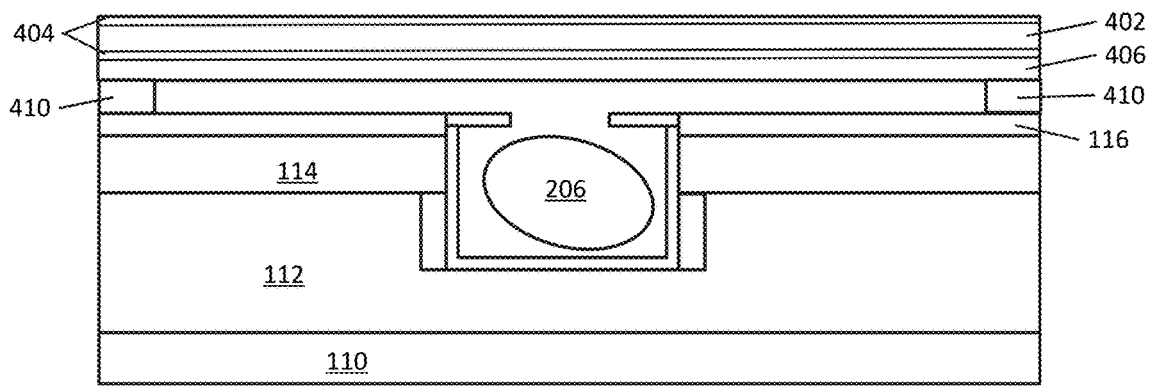
FIG. 4E is a cross-sectional diagram illustrating certain aspects of an embodiment of an abdominal wall module overlying an embodiment of a base unit and hernia model assembly having overlying spacer elements.

In a different embodiment, spacer elements are included between the base unit and the abdominal wall module. A simplified perspective view of a base unit with overlying spacer elements is shown in FIG. 4D. Spacer elements 410 can be formed from any suitable material, such as wood, plastic, or cardboard. In an embodiment, spacer elements 410 are attached to underlying and overlying layers in a removable fashion, such as snaps, hook-and-loop fasteners, tape, or non-permanent adhesive. A cross-sectional view of an abdominal wall module overlying a base unit with intervening spacer elements is shown in FIG. 4E. Use of spacer elements such as elements 410 may be useful in providing space for working with surgical instruments during simulated procedures using the hernia training model. The spacer elements may also simulate expansion caused by air or gas insufflation during a surgical procedure.

Multiple variations and modifications of the abdominal wall module embodiments described herein will be apparent to those of ordinary skill in the art in view of this disclosure. For example, some of the layers shown herein could be combined together or omitted in some embodiments. Desired layer thicknesses may vary significantly depending on the age, size and other characteristics of a simulated patient, or on the specific abdominal location of a particular hernia. Layers shown here as a single layer could also be represented using combinations of multiple material layers. As an example, additional and/or thicker simulated fat layers may be used in an embodiment designed to represent an obese patient.

In an embodiment, an abdominal wall module as described herein is supplied as a component of a hernia training model. The abdominal wall module can also be supplied separately as a replacement part. In some embodiments, individual layers of an abdominal wall module may be supplied as replacement parts. An abdominal wall module as described herein may also be used apart from a hernia training model, in, for example, a cutting or suture trainer.

Cutaneous Module

Figure 5A:
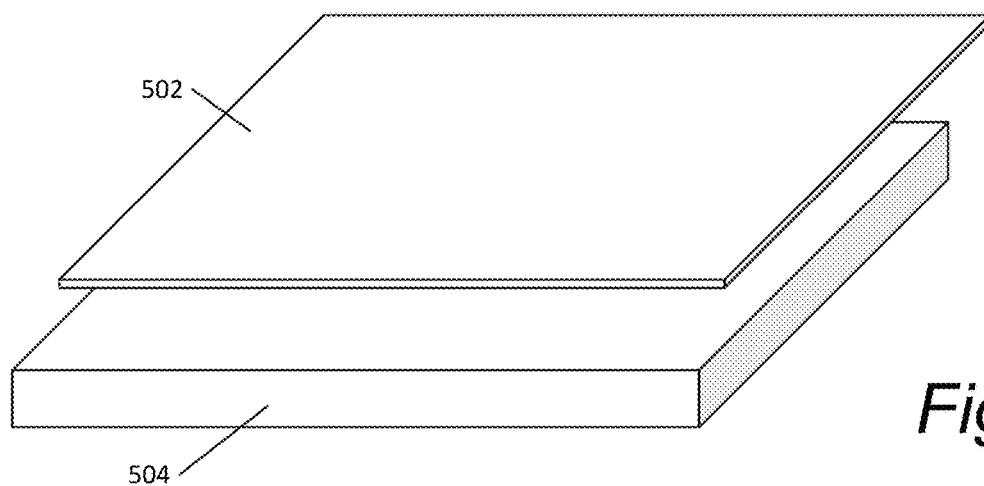
FIG. 5A is a diagram illustrating component layers of an embodiment of a cutaneous module for a ventral hernia anatomy training model.
Figure 5B:
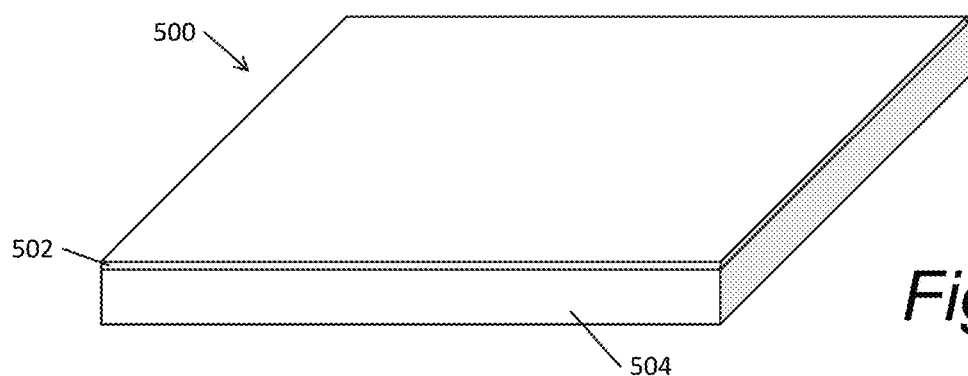
FIG. 5B is a diagram illustrating certain aspects of an embodiment of a cutaneous module for a ventral hernia anatomy training model.
Figure 5C:
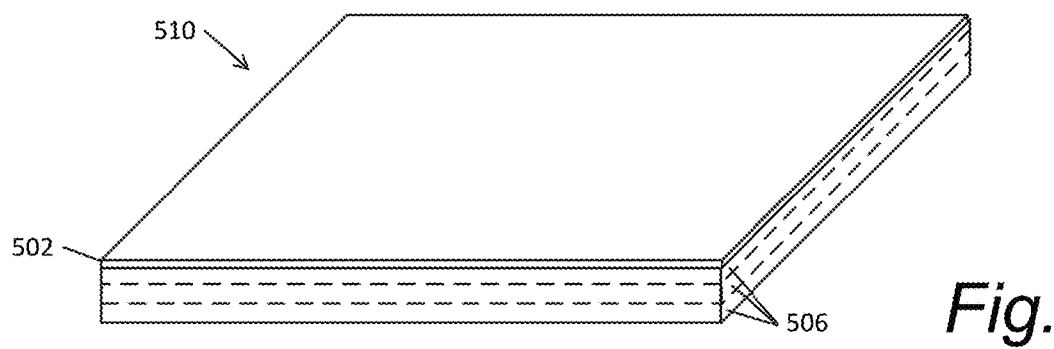
FIG. 5C is a diagram illustrating certain aspects of another embodiment of a cutaneous module for a ventral hernia anatomy training model.

Perspective views of an embodiment of a cutaneous module for a hernia training model are shown in FIGS. 5A-5C. In this embodiment, cutaneous module 500 has two component layers. The layers are separated for clarity in the exploded view of FIG. 5A, and shown attached to one another in the view of FIG. 5B. Upper layer 502 is a skin simulation layer, and is formed from a relatively flexible material that can be cut and sutured using appropriate surgical instruments. In an embodiment, layer 502 is made using a relatively thin layer of a material that simulates human skin texture. For example, a vinyl or simulated leather material may be used in some embodiments. Other flexible materials may be used in other embodiments, including but not limited to flexible foam layers, fabrics or leathers. In an embodiment, skin simulation layer 502 is formed from a material resistant to water and/or other liquids. Such an embodiment may facilitate practicing of pre-operation sterilization procedures. In an alternate embodiment, a fluid-resistant overlay, such as a plastic film layer, may be used to practice such pre-operation sterilization procedures, and then removed before continuing with a hernia repair simulation. In an embodiment, layer 502 has a thickness comparable to that of a skin layer. In a further embodiment, layer 502 has a thickness of approximately one millimeter or less. In an embodiment, layer 502 has a color similar to that of a human skin layer. In a further embodiment, layer 502 is available in a range of colors approximating human skin tones.

Layer 504 is a fat simulation layer. In an embodiment, layer 504 simulates a subcutaneous fat layer. In an embodiment, layer 504 is formed from a flexible or supple material, such as, for example, a flexible foam sheet. In an embodiment, layer 504 has a thickness comparable to that of a patient's subcutaneous fat layer. In a further embodiment, layer 504 has a thickness of between approximately one millimeter and a few centimeters. In a still further embodiment, different versions of cutaneous module 500 are made available for simulations reflecting patients with varying amounts of body fat. In an embodiment, layer 504 has a color similar to that of a fat layer. In a further embodiment, layer 504 is formed from a yellow or yellowish material. In some embodiments, a layer such as simulated fat layer 504 is formed from multiple layers of relatively thinner material, as illustrated by layers 506 in cutaneous module 510 of FIG. 5C. Such a multilayer embodiment may be useful, for example, in low-cost implementations of a cutaneous module, so that various fat layer thicknesses can be implemented using a single type of layer material.

The component layers of cutaneous module 500 are attached to one another to form a stack, as illustrated by FIG. 5B. In an embodiment, the layers are attached at one or more points at or near the lateral perimeter of module 500, and are not bonded together in the central part of the module. In some embodiments, one or more of the layers are attached together in a removable fashion, such as by hook-and-loop fasteners or non-permanent adhesives. Such removable attachment may be useful in embodiments where adding spacer elements between layers is desired. Adding spacer elements between layers can be used to simulate expansion caused by insufflation during a surgical procedure, as discussed further above in connection with FIGS. 4D and 4E. In other embodiments, one or more of the layers are attached together in a more permanent fashion, such as stapling, stitching, and heat and/or compression bonding.

Figure 5D:
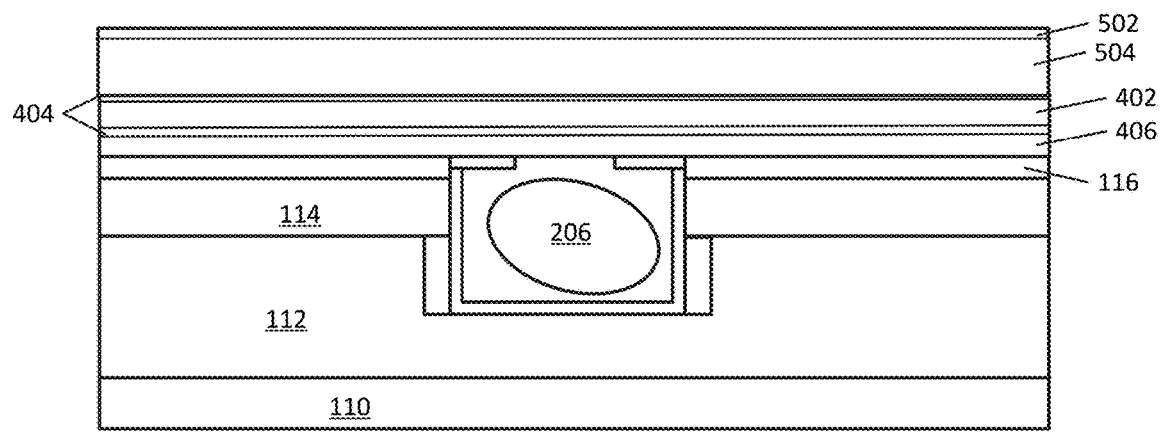
FIG. 5D is a cross-sectional diagram illustrating certain aspects of an embodiment of a cutaneous module combined with embodiments of an abdominal wall module, base unit, and hernia model assembly.

A simplified cross-sectional view of cutaneous module 500 overlying the abdominal wall module, base unit and hernia model assembly of FIG. 4C is shown in FIG. 5D. In a similar manner as described for the components in FIG. 4C, the lower surface of cutaneous module 500 is, in an embodiment, directly attached to the upper surface of the underlying abdominal wall module. In a further embodiment, the cutaneous module is attached to the abdominal wall module in a removable fashion, such as using snaps, hook-and-loop fasteners, tape, or non-permanent adhesive. Alternatively, spacer elements may be included between cutaneous module 500 and the abdominal wall module, in a similar manner as discussed above in connection with FIGS. 4D and 4E.

Multiple variations and modifications of the cutaneous module embodiments described herein will be apparent to those of ordinary skill in the art in view of this disclosure. For example, some of the layers shown herein could be combined together or omitted in some embodiments. Desired layer thicknesses may vary significantly depending on the age, size, body mass index, and other characteristics of a simulated patient, or on the specific abdominal location of a particular hernia. Layers shown here as a single layer could also be represented using combinations of multiple material layers.

In an embodiment, a cutaneous module as described herein is supplied as a component of a hernia training model. The cutaneous module can also be supplied separately as a replacement part. In some embodiments, individual layers of a cutaneous module may be supplied as replacement parts. A cutaneous module as described herein may also be used independently from a hernia training model, as for example, a cutting or suture trainer. In an embodiment, the uppermost skin simulation layer may be extended or wrapped around the sides of the cutaneous module and attached to the lower surface of the lowest layer of the module. For the cutaneous module, as for other modules and components described herein, any or all of the component layers are in some embodiments formed from liquid-resistant materials.

Use of Ventral Hernia Training Model

In an embodiment, use of a ventral hernia training model begins with a stack of elements and modules similar to that illustrated by FIG. 5D. Use may begin with appreciating (in the sense of recognizing or discerning) any external landmarks and orientation of the patient, which may be provided by tactile exploration of the top skin layer and confirmed by a clear plastic overlay with orientations/landmarks explicitly marked. Pre-operative preparation may be executed as well. The skin and subsequent layers may be intact and a hernia may or may not be appreciated or discerned from the top skin layer depending on the hernia size and type and the body mass index of the patient. In a further embodiment, with reference to the structure of FIG. 5D, an opening is formed in one or more of layers 402, 404 and 406, and model hernia 206 is extended out of the base unit cavity and at least partially through this opening in the abdominal wall module layers. Continuing with reference to the layers designated in FIG. 5D, the top of the training model presents the substantially smooth surface of upper skin simulation layer 502. In an embodiment, a palpable "bump" is present at the upper surface as a result of the extension of hernia model 206 upward from its cavity. In such an embodiment, use of the training model may include practice in identifying or diagnosing a hernia through palpation of the upper surface of the training model. In some embodiments, a visible feature such as a navel or a scar may be drawn onto the skin simulation layer, or onto a transparent overlay employed for this purpose. Such visual features may assist with practice in diagnosis or in orientation of the training model area with respect to a simulated patient's body.

Use of the hernia training model may also include practice of preoperational procedures such as sterilization techniques (using, for example, BETADINE® or another antiseptic solution), local numbing techniques (for example, using an injection) or draping techniques. As noted above, in some embodiments the skin simulation layer is formed from a liquid-resistant material to prevent damage from practicing with antiseptic solutions or other liquids. In some embodiments, a liquid-resistant layer can be temporarily interposed beneath the skin simulation layer to protect underlying layers from, for example, injected liquids. In an embodiment, the upper surface area of the hernia training model corresponds to the area of a patient's skin exposed by a preoperative draping procedure.

After any preoperational procedures, a simulated hernia repair procedure begins with cutting through the skin simulation layer using an appropriate surgical instrument. Appropriate surgical instruments and techniques will be apparent to those of ordinary skill in the art of hernia repair surgery; it is anticipated that the hernia training model described herein is used by surgical trainees familiar with the procedures being practiced, or at least under the supervision of skilled practitioners. Using the training model embodiment of FIG. 5D, the cut through skin simulation layer 502 exposes underlying fat simulation layer 504. Layer 504 is then cut through or otherwise separated using appropriate instruments, including but not limited to cauterization instruments. In an embodiment, cut or separated edges of layers 502 and 504 are pulled back and held using clamps or other suitable instruments.

Formation of an opening in layer 504 exposes the underlying abdominal wall module. In embodiment in which setting up the hernia training model for a simulated operation includes forming an opening in the abdominal wall module and extending the hernia model through the opening, exposure of the abdominal wall module should make the hernia model at least partially visible. Additional separation and retraction, possibly involving additional cutting, of the layers of the abdominal wall module is performed as needed to obtain sufficient access to the hernia model. In an embodiment, the layers as shown in FIG. 5D are separated and retracted one by one: upper simulated fascia, simulated muscle, lower simulated fascia, and simulated fat layer.

Specific hernia repair procedures may vary based on considerations such as the type and severity of the hernia, other patient indications or contraindications, and local practice. As a general matter, the hernia is typically "reduced" by pushing it back below the abdominal wall. In some embodiments, the hernia is reduced in size as well. Hernia coverings, which may be simulated in the hernia training model using a flexible overlying portion of a container upper surface 204 and/or a hernia sac 210, may be cut away in some embodiments. In some embodiments, a portion of the hernia contents may be removed as well. For example, a portion of the hernia model configured to simulate omentum may be cut away in some embodiments of the simulated hernia repair procedure. In some cases, hernia repair includes using a piece of a mesh material to help repair or strengthen the abdominal wall after the hernia is reduced. The simulated repair procedure may therefore include placement of a piece of mesh within or alongside the abdominal wall module so that the defect (opening) in an abdominal wall fascia is covered by the mesh. In an embodiment, the specific layers the mesh is inserted alongside depends on the specific technique being employed, or may be a matter of practitioner judgement depending on conditions encountered. If the procedure being simulated includes suturing an inserted mesh piece into place, suturing of the mesh to the desired layer(s) of the ventral hernia model is performed.

After the hernia repair portion of a simulated procedure is performed, the separated layers of the hernia training model are closed and sutured pursuant to the requirements of the procedure being simulated. In an embodiment, the cutaneous module is removed from the hernia training model after the simulated hernia repair procedure is completed. The removed cutaneous module can be replaced with a fresh (uncut) cutaneous module for practicing a new procedure. In addition to replacing the cutaneous module, performing a new procedure using the same hernia training model would in some embodiments require removing any mesh added to the abdominal wall module, and resetting the hernia model in its extended position above the base unit cavity. Cut-away portions of the hernia model, such as, for example, simulated omentum or a simulated hernia sac, would be replaced as well in some embodiments. It is believed that the modular nature of the hernia training model allows such consumable components to be replaced efficiently and economically.

In an embodiment, training materials are supplied with the hernia training models described herein. In a further embodiment, training materials supplied include video demonstration materials. In some embodiments, storage media including training materials, whether digital storage materials or paper instructions, are stored in a slot or compartment included in the base unit of a ventral hernia training model. Such digital storage media may include, for example, disks configured for insertion into a computing device's disk drive or storage devices configured to connect to an interface of a computing device, such as a Universal Serial Bus (USB) interface. In some embodiments, a link or address usable to access training materials over a network such as the Internet is provided with a hernia training model. Such a link or address is printed onto a portion of the hernia training model, such as a base unit, in some embodiments. Such a link or address could be printed alphabetically in some embodiments. Alternatively or in addition, a link or address could be encoded in a symbol such as a Quick Response (QR) code readable using a "smartphone" or other computing device.

Multiple variations and modifications of the ventral hernia training model embodiments described herein will be apparent to those of ordinary skill in the art in view of this disclosure. For example, the component modules described herein can be split into additional submodules or combined into fewer modules in some embodiments. Any or all of the components, layers and modules described herein can be made liquid-resistant in some embodiments, for example through coating or covering with a liquid-resistant material. Any or all of the components and layers described herein can be implemented in a low-cost manner in some embodiments, using commonly available items or materials. The exact procedures to be simulated using embodiments of the ventral training model may vary depending on factors such as hernia type and severity, other patient indications or contraindications, local practices, and research advances. The modular and configurable nature of the training model embodiments described herein are believed to accommodate a wide variety of procedure simulation scenarios.

Groin Hernia Training Model

Hernias in the groin area include inguinal hernias associated with the inguinal canal and femoral hernias associated with the femoral artery and femoral canal. The groin hernia training model embodiments described herein are primarily directed toward simulation of inguinal hernia repair. However, the training model is believed to be readily configurable for simulation of other hernia types, including femoral hernias, as well.

Figure 6:
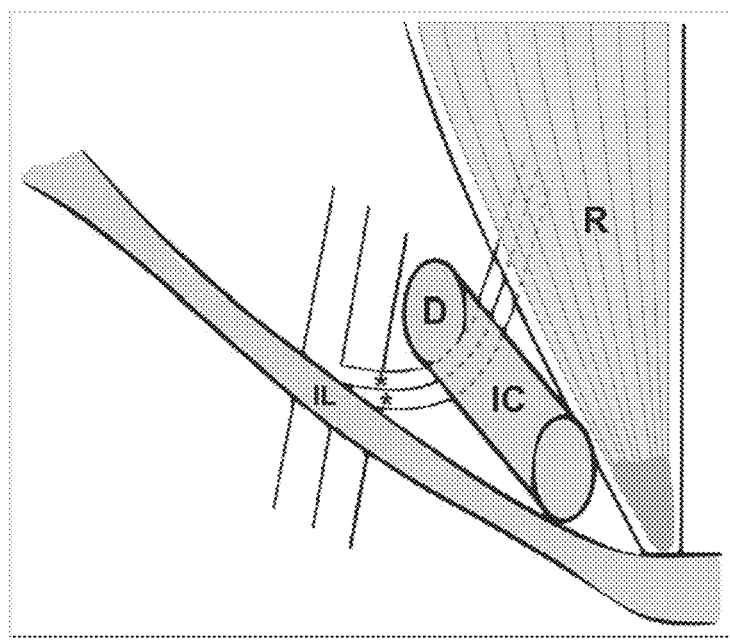
FIG. 6 is a diagram illustrating certain features of groin anatomy relevant to a groin hernia.

Many of the characteristics described above for the ventral hernia training model, such as modular design, configurability and material choices, are also applicable to the groin hernia training model embodiments described herein. Certain differences in the configuration of the groin hernia training model as compared to the ventral hernia training model reflect the respective anatomical environments being simulated. A simplified view of certain relevant features of the groin anatomy is shown in FIG. 6 (drawing from Philip Yoong et al., "The inguinal and femoral canals: A practical step-by-step approach to accurate sonographic assessment," *Indian J. Radiol. Imaging* 23(4), pp. 391-95, October-December 2013). The view of FIG. 6 is oriented as a top view of a patient's right-side groin region, with the patient's head in the direction above the top of the drawing, and feet in the direction below the bottom of the drawing. In the diagram of FIG. 6, the rectus abdominis muscle is labeled "R," the inguinal ligament is labeled "IL," the inguinal canal is labeled "IC," the deep inguinal ring is labeled "D" and the inferior epigastric vessels (artery and vein) are denoted with asterisks (*).

Base Unit

Figure 7A:
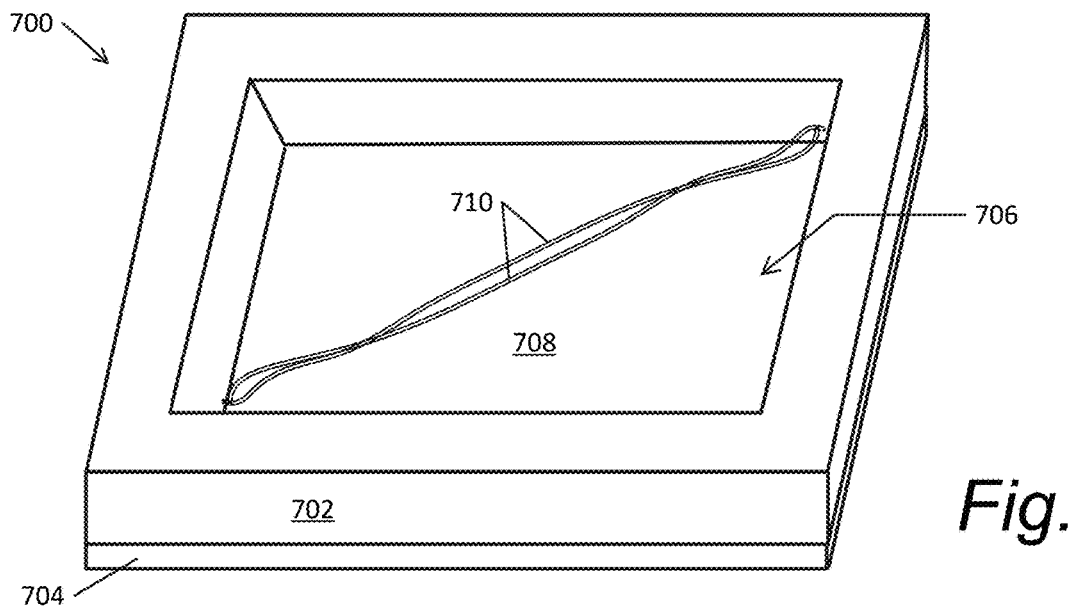
FIG. 7A is a diagram illustrating certain features of an embodiment of a cavity structure component of a base unit for a groin hernia anatomy training model.
Figure 7B:
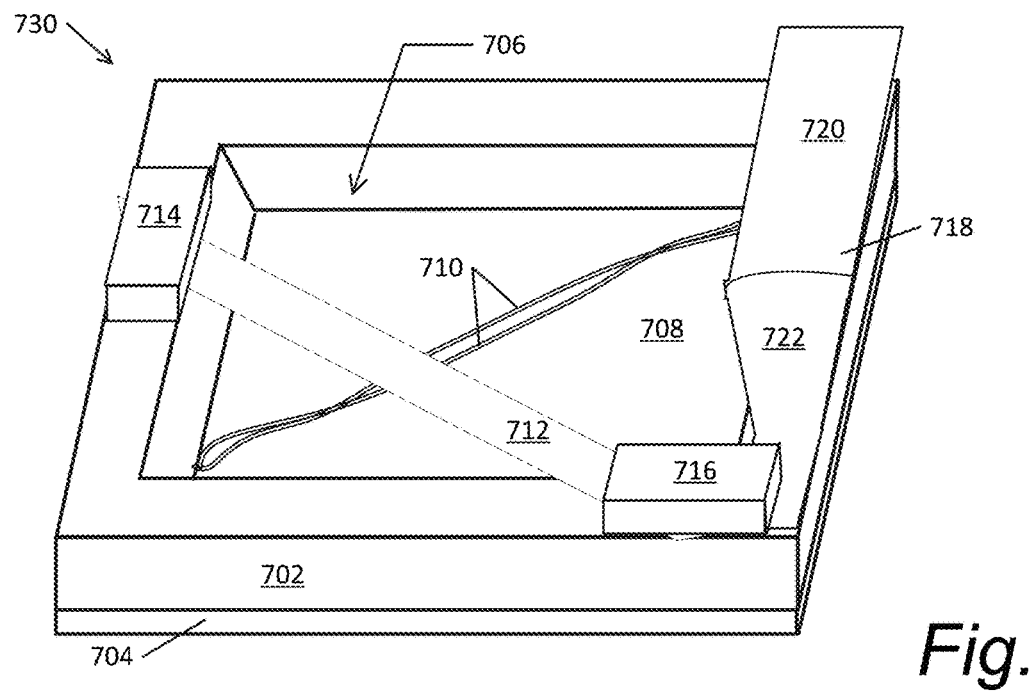
FIG. 7B is a diagram illustrating certain features of an embodiment of a base unit for a groin hernia anatomy training model.

Embodiments and components of a base unit for a groin hernia training model are illustrated in FIGS. 7A-7B. FIG. 7A illustrates an embodiment of a cavity structure component of a base unit for a groin training model. In the embodiment of FIG. 7A, cavity structure 700 includes a frame 702 and floor panel 704, joined together such that a rectangular cavity 706 having a floor 708 is formed. In other embodiments, the frame and floor portions may be implemented as a single monolithic element, or as a combination of a larger number of elements. In some embodiments, cavity 706 and/or cavity structure 700 may have a shape, or "footprint", other than rectangular, such as a circular or elliptical shape. In an embodiment, an area subtended by cavity structure 700 approximates an area of a patient's skin exposed by a patient drape used during surgery.

In an embodiment, the frame and floor portions of cavity structure 700 are made from a substantially rigid material such as wood, rigid plastic, metal, rigid cardboard, an extruded polystyrene such as STYROFOAM®, any other material suitable for formation of a substantially rigid cavity structure, or any combinations of such materials. In an embodiment, cavity structure 700 is made using one or more materials with sufficient mass that a base unit incorporating the cavity structure can be expected to remain stationary during training sessions. Cavity structure 700 may in some embodiments include a fixation or gripping mechanism on its lower surface, in a similar manner to embodiments of the ventral hernia training model base unit described above. In an example of an embodiment using readily available materials, the frame and floor portions of cavity structure 700 are made using precut wooden elements such as plaques and frames. Cavity 706 of cavity structure 700 allows deeper anatomical structures such as blood vessels and fascial layers of the inguinal region to be incorporated. In an embodiment, a cavity may be created by forming a layer on top of a flat base board and then removing material to create the recess or cavity.

At or near floor 708 of cavity 706, simulated inferior epigastric vessels 710 are disposed. In an embodiment, two simulated vessels 710 are implemented using different colors to represent an inferior epigastric artery and vein, respectively. Although shown in somewhat separated positions for clarity in FIG. 7A, simulated inferior epigastric vessels 710 are coupled more closely together in some embodiments. In a further embodiment, both epigastric vessels are simulated using a single structure. In yet another embodiment, a different number of inferior epigastric vessels is represented, such as, for example, three vessels including one artery and two veins. In the embodiment of FIG. 7A, the ends of simulated vessels 710 are attached to interior sidewalls of frame 702. In an alternative embodiment, one or both of the ends is instead attached to floor 708 of cavity 706. Although shown in FIG. 7A as attached to adjacent sidewalls of frame 702, the ends of simulated vessels 710 may also be attached to opposing sidewalls of frame 702 in some embodiments. In an embodiment, the specific attachment points of the ends of simulated vessels 710 depends upon details of, for example, the anatomy being simulated, the type of hernia being simulated, and/or the specific procedure being practiced. In an embodiment, one or more attachment structures within cavity 706 are provided for attachment of each end of simulated vessels 710. Such attachment structures may take various forms, including but not limited to snap fasteners, hooks or loops. In a further embodiment, ends of simulated vessels 710 may include hooks or other structures to facilitate attachment to attachment structures within cavity 706. Ends of simulated vessels 710 may also be attached using any other suitable attachment means, including but not limited to staples or adhesives.

An additional embodiment of cavity structure 700 may also include simulated femoral (or iliac) vessels, or portions thereof, within cavity 706. In one such embodiment, the simulated femoral vessels are situated near the lower left-hand corner of cavity floor 708, and the left-side ends of simulated inferior epigastric vessels 710 are coupled to their respective simulated femoral vessels, rather than being attached to a sidewall of cavity 706. An embodiment of an arrangement of simulated femoral vessels and simulated inferior epigastric vessels 710 may be generally similar to that depicted in FIG. 6 above. Embodiments including simulated femoral vessels may allow the groin hernia training model to simulate a femoral hernia, instead of or in addition to simulation of inguinal hernias as described further below.

In an embodiment, simulated inferior epigastric vessels 710 are formed from an elongated structure or material, having a generally filamentary shape. Such materials may include, without limitation, threads, strings, yarns, plastic cording, wires, flexible tubing, or combinations of these. In some embodiments, simulated vessels 710 are arranged to follow an approximately straight line across floor 708 of cavity 706. In other embodiments, simulated vessels 710 are arranged to follow a more curved or otherwise nonlinear path. In a further embodiment, simulated vessels 710 arranged to follow a nonlinear path are formed using materials or structures capable of holding a shape, such as wire-containing materials or structures. Examples of wire-containing materials or structures include, without limitation, insulated wires or cables or structures such as pipe cleaners. In another embodiment, simulated vessels 710 arranged to follow a nonlinear path are formed using materials incapable of holding a shape, such as some strings or yarns, but are held in place using multiple attachment points along floor 708, or using a continuous attachment method such as an adhesive.

In an alternative embodiment, simulated inferior epigastric vessels 710 are drawn, painted, printed, or otherwise depicted upon floor 708 of cavity 706, rather than being simulated using filamentary structures or materials. In a further embodiment, vessels 710 are depicted using a "puffy" paint or other textured substance (including but not limited to caulking substances) in order to simulate the thickness of actual arteries and veins. In another embodiment, depictions of epigastric vessels are made on removable substrates or films that may be interchangeably placed upon floor 708 of cavity 706.

In an embodiment such as that described above including simulated femoral vessels, the simulated femoral vessels may be formed from similar materials as those described above for simulated inferior epigastric vessels. In an embodiment, the simulated femoral vessels are significantly larger in diameter than the simulated inferior epigastric vessels, and are accordingly formed from larger-diameter materials or structures. In some embodiments in which simulated vessels are in tubular form, the simulated vessels include fittings for causing fluid to flow through the simulated vessels to simulate blood flow. Such an embodiment may allow more realistic simulation of procedures such as artery or vein ligation.

Any or all of the components of cavity structure 700 may be formed from or coated with liquid-resistant materials. In an embodiment, a liquid-resistant cover, such as a clear plastic film, is fitted over cavity structure 700 during use within a groin hernia training model. In a further embodiment, such a liquid-resistant cover is situated above floor 708 but below structures such as simulated inferior epigastric vessels 710.

An embodiment of a base unit 730 incorporating cavity structure 700 is shown in FIG. 7B. Extending across the top of cavity 706, in a lateral direction generally transverse (though not necessarily perpendicular) to that of simulated vessels 710, is simulated inguinal ligament 712. In an embodiment, simulated inguinal ligament 712 is formed from a flexible material having a ribbon-like shape. In a further embodiment, simulated inguinal ligament 712 is formed from a piece of flat elastic. In other embodiments, simulated ligament 712 is formed from another material or structure, including without limitation tapes, straps or belts made from plastics, fabrics, natural rubber or synthetic rubber. In an embodiment, simulated inguinal ligament 712 has a color similar to that of the ligament it simulates. In a further embodiment, simulated ligament 712 is formed from a white or similarly light-colored material. Although shown in FIG. 7B as extending in a substantially straight line, simulated inguinal ligament 712 is in some embodiments arranged to follow a slight curve.

In the embodiment of FIG. 7B, simulated inguinal ligament 712 is attached to upper surfaces of adjacent sides of frame 702. This attachment may be achieved through any suitable attachment means, several of which are described within this disclosure. As one example, simulated inguinal ligament 712 may be attached to frame 702 using hook-and-loop fasteners such as VELCRO®. Blocks 714 and 716 are attached to frame 702 above respective ends of simulated ligament 712. Like simulated ligament 712, blocks 714 and 716 can be attached to frame 702 and/or an upper surface of simulated ligament 712 using any suitable attachment means. In an embodiment, attachment of blocks 714 and 716 helps to hold simulated ligament 712 in place. Alternatively or in addition to helping to hold simulated ligament 712 in place, block 714 in some embodiments simulates the topography of the anterior superior iliac spine (ASIS). Similarly, block 716 in some embodiments simulates the topography of the pubic tubercle. In an embodiment, blocks 714 and 716 are formed from a relatively hard material, including but not limited to wood, metal, or hard plastic. Although shown in FIG. 7B as having simple rectangular block shapes, "blocks" 714 and 716 may in an embodiment have more irregular shapes. In a further embodiment, blocks 714 and 716 may be formed, at least on their upper surfaces, into shapes that more closely approximate those of the ASIS and pubic tubercle, respectively.

Attached to the top of and extending along the right side of frame 702, in the embodiment of FIG. 7B, is simulated rectus abdominis portion 718. In the embodiment of FIG. 7B, simulated rectus abdominis portion 718 includes an upper portion 720 and lower portion 722. In an embodiment upper portion 720 has a color approximating that of a muscle. In a further embodiment, upper portion 720 has a red or reddish color. Lower portion 722, in an embodiment, has a color approximating that of aponeuroses or sheath structure passing in front of a rectus abdominis muscle as it approaches the pubic bone. In a further embodiment, lower portion 722 has a white or similarly light color. In an embodiment, the upper surface of simulated rectus abdominis portion 718 is higher at the upper end of the right side of frame 202 (the end of simulated portion 718 including upper portion 720) and lower at the lower end of portion 718 (including lower portion 722) approaching block 716. Such an embodiment may simulate the slope of an actual rectus abdominis muscle as it approaches its connection point on the pubic bone. Such an elevation of the upper part of simulated portion 718 may in an embodiment be achieved using one or more underlying blocks similar to blocks 714 and 716. Alternatively or in addition, a variation in elevation may be achieved by forming the upper portion of simulated rectus abdominis portion 718 from a thicker material or combination of materials.

In an embodiment, simulated rectus abdominis portion 718 is formed from one or more materials having some degree of compressibility, such as one or more layers of a flexible foam material. Color variations may be achieved in some embodiments using adhesive-backed paper or plastic film materials. Base unit 730 of FIG. 7B is configured for simulation of the groin region on a patient's right side. In other embodiments, a base unit is configured for simulation of the groin region on a patient's left side. In a further embodiment, a base unit is configurable to simulate either side of a patient. In one such embodiment, a base unit is supplied with two simulated rectus abdominis portions 718 having mirror-image configurations. Such an embodiment may also have alternate connection points for connection of simulated vessels 710, depending on which side of the patient is being simulated. A reconfigurable embodiment may also have alternative attachment positions for simulated ligament 712 and blocks 714 and 716, depending on which side of the patient is being simulated.

Abdominal Wall Module

The abdominal wall in the groin region includes a combination of various muscles and fascia, with openings for passage of various structures including certain arteries and ligaments and, in males, the spermatic cord. In an embodiment of the groin hernia training model, the abdominal wall is represented by a lower layer arranged below (or more interior to, in a simulated patient) simulated inguinal ligament 712 and an upper layer arranged above simulated inguinal ligament 712. Additional layers may be included in other embodiments, depending on the degree of anatomical detail required for a given training procedure. In some embodiments, a layer within the abdominal wall module may be configured to have distinct portions representing, for example, distinct muscle or fascia regions, depending on the degree of anatomical detail required.

Figure 8A:
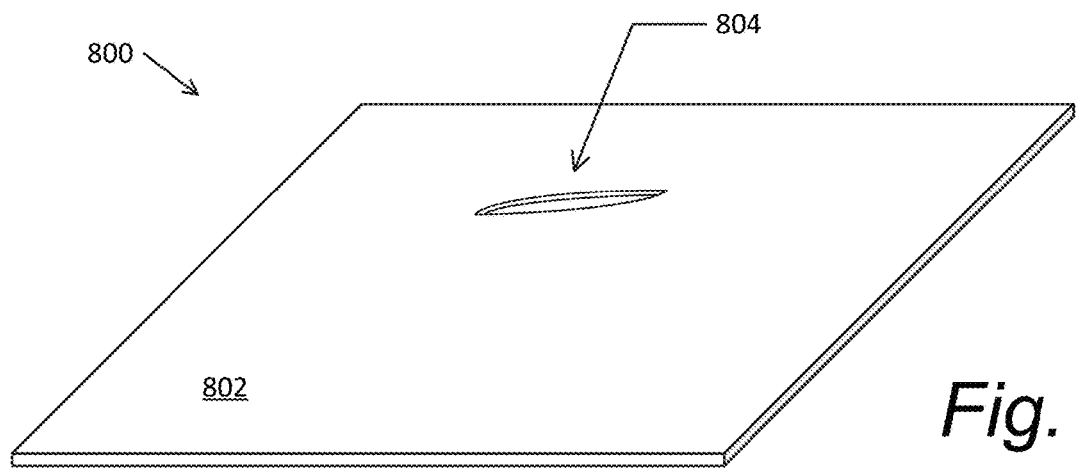
FIG. 8A is a diagram illustrating certain features of an embodiment of a lower layer of an abdominal wall module for a groin hernia anatomy training model.

An embodiment of a lower layer 800 of an abdominal wall module is illustrated in FIG. 8A. Layer 800 includes simulated muscle/fascia layer 802 having an opening 804. In an embodiment, simulated muscle/fascia layer 802 represents, at least in part, the transversalis fascia. Opening 804, in an embodiment, represents the deep inguinal ring in the transversalis fascia. Simulated muscle/fascia layer 802 is formed in some embodiments from one or more flexible materials similar to those described elsewhere herein for other simulated muscle and/or fascia layers. For example, fabric, flexible foam, mesh, paper or combinations of these may be used in some embodiments. In an embodiment, simulated muscle/fascia layer 802 is formed from a material capable of being cut in order to simulate natural openings or defects in the abdominal wall. In a further embodiment, simulated muscle/fascia layer 802 is formed from a material capable of being sutured in a manner similar to suturing of a muscle or fascia layer in a patient. Opening 804 is formed in some embodiments by a slit in layer 802.

Figure 8B:
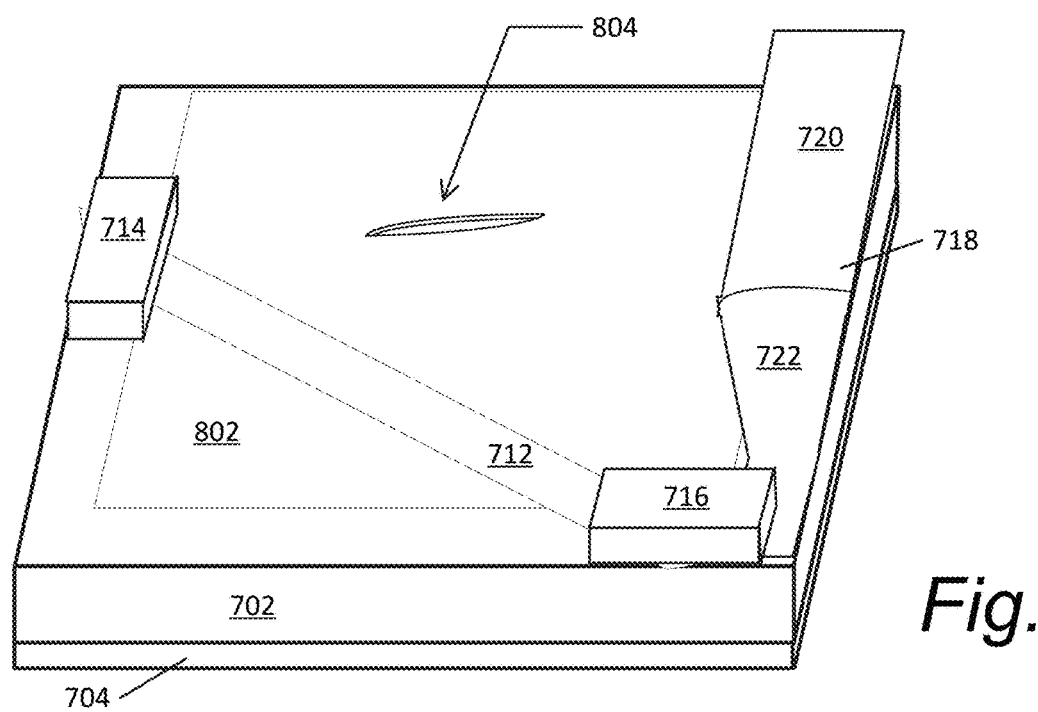
FIG. 8B is a diagram illustrating certain features of an embodiment of a lower layer of an abdominal wall module arranged upon an embodiment of a base unit.

A simplified perspective view of an embodiment of lower layer 800 arranged upon base unit 730 (of FIG. 7B) is shown in FIG. 8B. In the embodiment of FIG. 8B, simulated muscle/fascia layer 802 is positioned over cavity 706 of base unit 730 and below simulated inguinal ligament 712. In an embodiment, the lower surface of layer 802 is attached to the upper surface of frame 702 at one or more locations around the outer edge of the lower surface of layer 802. In a further embodiment, attachment of layer 802 to the upper surface of frame 702 is by some non-permanent attachment mechanism, such as those described elsewhere herein (including, for example, snaps, hook-and-loop fasteners or nonpermanent adhesives).

Figure 9A:
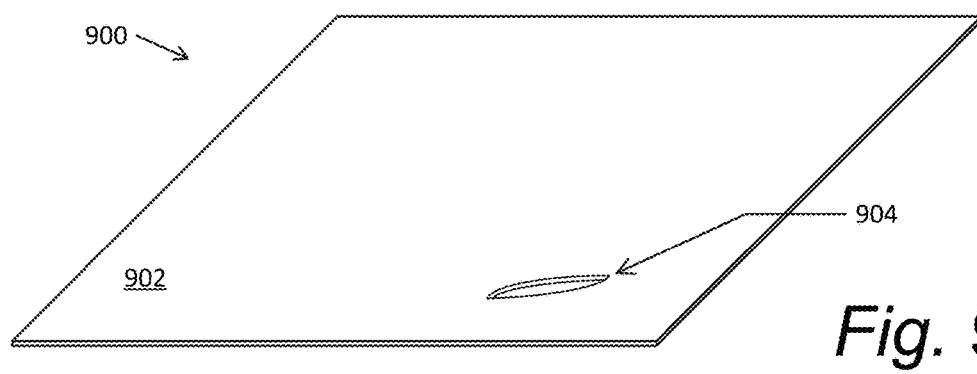
FIG. 9A is a diagram illustrating certain features of an embodiment of an upper layer of an abdominal wall module for a groin hernia anatomy training model.

An embodiment of an upper layer 900 of an abdominal wall module is illustrated in FIG. 9A. Layer 900 includes simulated muscle/fascia layer 902 having an opening 904. In an embodiment, simulated muscle/fascia layer 902 represents, at least in part, the aponeurosis of the external oblique muscle. Opening 904, in an embodiment, represents the superficial, or external, inguinal ring in the aponeurosis of the external oblique. Simulated muscle/fascia layer 902 is formed in some embodiments from one or more flexible materials similar to those described elsewhere herein for other simulated muscle and/or fascia layers. For example, fabric, flexible foam, mesh, paper or combinations of these may be used in some embodiments. In an embodiment, simulated muscle/fascia layer 902 is formed from a material capable of being cut in order to simulate natural openings or defects in the abdominal wall. In a further embodiment, simulated muscle/fascia layer 902 is formed from a material capable of being sutured in a manner similar to suturing of a muscle or fascia layer in a patient. Opening 904 is formed in some embodiments by a slit in layer 902.

Figure 9B:
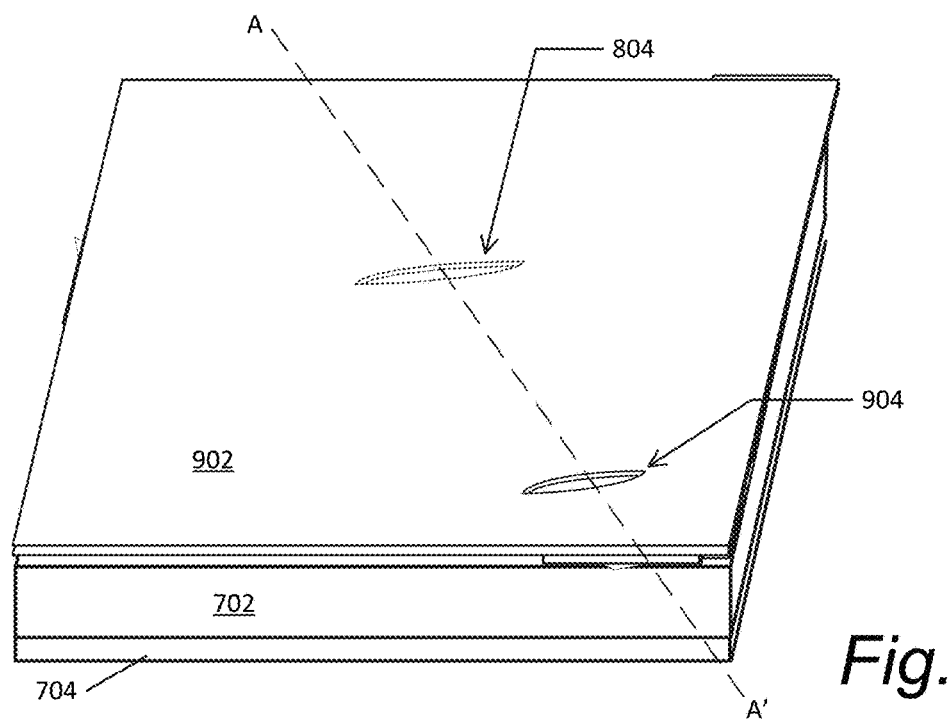
FIG. 9B is a diagram illustrating certain features of an embodiment of an upper layer of an abdominal wall module arranged over an embodiment of a lower layer of the abdominal wall module and upon an embodiment of a base unit.

A simplified perspective view of an embodiment of upper layer 900 arranged over lower layer 800 on base unit 730 is shown in FIG. 9B. In the embodiment of FIG. 9B, simulated muscle/fascia layer 902 is positioned over the entirety of base unit 730, including simulated inguinal ligament 712. In an embodiment, the lower surface of layer 902 is attached to the upper surface of frame 702 and/or to an upper surface of lower layer 802 at one or more locations around the outer edge of the lower surface of layer 902. In a further embodiment, attachment of layer 902 to an underlying layer or surface is by some non-permanent attachment mechanism, such as those described elsewhere herein (including, for example, snaps, hook-and-loop fasteners or nonpermanent adhesives). Although typically not visible through layer 902, underlying opening 804 of layer 800 is shown using dotted lines to indicate its location.

Figure 9C:
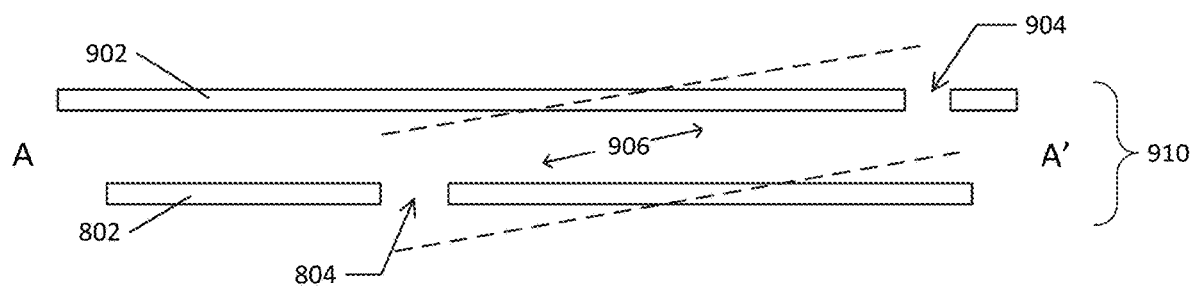
FIG. 9C is a cross-sectional diagram illustrating relative positioning of an upper layer and lower layer of an abdominal wall module as arranged upon and over a base unit.

A simplified cross-sectional view of a cut along line A-A' of FIG. 9B of layers 802 and 902 is shown in FIG. 9C. The combination of layers 802 and 902 forms abdominal wall module 910 in the embodiment of FIG. 9C. In an embodiment, the region between layers 802 and 902 and between openings 804 and 904 serves as a simulated inguinal canal 906 (denoted generally by dashed lines). Simulated inguinal canal 906 is discussed further below in connection with embodiments of a simulated spermatic cord module and simulated hernia module. Although shown as flat layers in the simplified depictions of FIGS. 8 and 9, layers 802 and 902 are, in an embodiment, flexible layers, and as such may to some degree sag downwards and/or conform to the topography of underlying layers. In a further embodiment, simulated inguinal canal 906 is "closed" by virtue of contact between layers 802 and 902 unless a structure such as a simulated spermatic cord module is situated within the simulated inguinal canal.

An abdominal wall module such as module 910 of FIG. 9C can be made available in some embodiments as a component of and/or replacement part for a groin hernia training model. Alternatively or in addition, individual layers within an abdominal wall module are independently made available in some embodiments. In some embodiments, an abdominal wall module includes one or more layers in addition to layers 800 and 900. Thicknesses of layers within an abdominal wall module are selected, in some embodiments, to reflect typical thicknesses of simulated muscle or fascia layers. Alternatively or in addition, one or more layers within an abdominal wall module may incorporate variations in thickness or composition within a layer. Such variations may in some embodiments better simulate particular muscles or fascia.

Instead of or in addition to openings 804 and 904 simulating internal and external inguinal rings, other openings in layers of an abdominal wall module may be formed. For example, in some embodiments an opening below and/or to the right of opening 804 may be formed in lower layer 800. In the arrangement of FIG. 8B, for example, such an opening may be closer to simulated rectus abdominis muscle 718 and/or closer to block 716 than opening 804. An opening in this area may simulate an abdominal wall defect associated with a direct inguinal hernia. As another example, an opening in the lower portion of layer 800 may be formed in some embodiments. In the arrangement of FIG. 8B, for example, such an opening may be made on the opposite side of simulated inguinal ligament 712 than opening 804. An opening in this lower area may simulate the femoral ring. Such a simulated femoral ring may be formed in layer 800, for example, in certain embodiments in which simulated femoral vessels are formed within the underlying cavity of the base unit. In various embodiments, openings within layers of abdominal wall module 910 are formed by a user of the groin hernia training model, are formed in the abdominal module as-supplied, or include openings formed in both of these ways.

Spermatic Cord Module

Figure 10A:
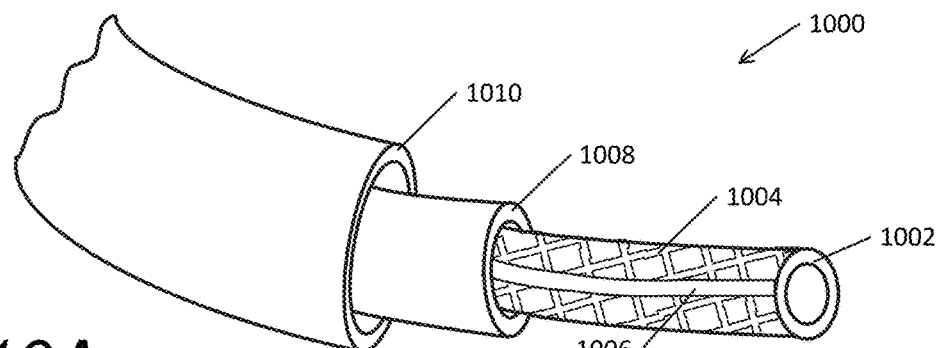
FIG. 10A is a diagram illustrating component layers of an embodiment of a spermatic cord module for a groin hernia anatomy training model.

Simplified perspective views illustrating a spermatic cord module for use with a groin hernia training model are shown in FIGS. 10A through 10D. FIG. 10A is an expanded view showing internal layers of a simulated spermatic cord 1000. In the embodiment of FIG. 10A, the innermost part of simulated spermatic cord 1000 is simulated vas deferens duct 1002. In an embodiment, simulated duct 1002 is formed from a flexible tube-shaped structure, such as a flexible plastic tubing. In an alternative embodiment, simulated duct 1002 is formed using a non-hollow structure, such as a flexible cord. In the embodiment of FIG. 10A, simulated venous plexus 1004 and simulated artery 1006 are disposed on the outer surface of simulated duct 1002. In an embodiment, simulated artery 1006 represents the testicular artery, or internal spermatic artery. In an embodiment, simulated venous plexus 1004 represents the pampiniform venous plexus. In some embodiments, structures 1004 and 1006 are drawn, painted, printed, or otherwise depicted on the outer surface of simulated duct 1002. Alternatively, one or both of structures 1004 and 1006 may be simulated using materials such as threads, strings, tubing or cords. Such structurally-simulated versions of simulated venous plexus 1004 and simulated spermatic artery 1006 may be attached to simulated duct 1002 in some embodiments, or may alternatively be situated alongside simulated duct 1002 without attachment. Additional simulated veins, vessels, nerves or other structures may be disposed at the outer surface of simulated duct 1002 in some embodiments, depending on the details of the anatomy being simulated and/or the level of anatomical detail required. In some embodiments, one or both of structures 1004 and 1006 may be omitted from the spermatic cord module.

Simulated spermatic cord 1000 further includes simulated inner sheath 1008 surrounding the outer sidewall of simulated duct 1002. In an embodiment, simulated inner sheath 1008 represents the internal spermatic fascia of a patient's spermatic cord. In an embodiment, simulated inner sheath 1008 is formed from a flexible tube-shaped structure. As in the case of other flexible structures described herein, suitable materials may include, without limitation, plastics, foams, fabrics, or combinations of such materials. In a further embodiment, simulated inner sheath 1008 is formed in a manner allowing a simulated hernia to be accommodated within it. For example, simulated inner sheath 1008 may be formed to have a large enough diameter, over at least part of its length, to accommodate a simulated hernia. Alternatively or in addition, simulated inner sheath 1008 may, as another example, be formed from a material having enough elasticity to stretch to accommodate a simulated hernia. In a still further embodiment, simulated inner sheath 1008 is formed from a material capable of being cut during a surgical simulation, or in order to simulate an opening or defect. In yet another embodiment, simulated inner sheath 1008 is formed from a material capable of being sutured in a manner similar to suturing of a muscle or fascia layer in a patient. Although not shown in FIG. 10A, simulated veins, arteries, nerves or other structures may be disposed at the outer surface of simulated inner sheath 1008 in some embodiments, depending on the details of the anatomy being simulated and/or the level of anatomical detail required. Such additional simulated structures may be depicted or formed in similar ways to those described above for structures 1004 and 1006.

Simulated spermatic cord 1000 of FIG. 10A further includes simulated outer sheath 1010 surrounding the outer sidewall of simulated inner sheath 1008. In an embodiment, simulated outer sheath 1010 represents a patient's cremasteric muscle and fascia. In an alternative embodiment, simulated outer sheath 1010 represents a patient's external spermatic fascia. In yet another embodiment, simulated outer sheath 1010 represents a combination of the external spermatic fascia and cremasteric muscle and fascia. In an alternative embodiment, one or more additional simulated sheath layers may be included in a spermatic cord module, depending on the details of the anatomy being simulated and/or the level of anatomical detail required. In an embodiment, simulated outer sheath 1010 is formed from a flexible tube-shaped structure. As for other flexible structures described herein, suitable materials may include, without limitation, plastics, foams, fabrics, or combinations of such materials. In a further embodiment, simulated outer sheath 1010 is formed in a manner allowing a simulated hernia to be accommodated within it. For example, simulated outer sheath 1010 may be formed to have a large enough diameter, over at least part of its length, to accommodate a simulated hernia. Alternatively or in addition, simulated outer sheath 1010 may, as another example, be formed from a material having enough elasticity to stretch to accommodate a simulated hernia. In a still further embodiment, simulated outer sheath 1010 is formed from a material capable of being cut during a surgical simulation, or in order to simulate an opening or defect. In yet another embodiment, simulated outer sheath 1010 is formed from a material capable of being sutured in a manner similar to suturing of a muscle or fascia layer in a patient. Although not shown in FIG. 10A, simulated veins, arteries, nerves or other structures may be disposed at the outer surface of simulated outer sheath 1010 in some embodiments, depending on the details of the anatomy being simulated and/or the level of anatomical detail required. Such additional simulated structures may be depicted or formed in similar ways to those described above for structures 1004 and 1006.

Figure 10B:
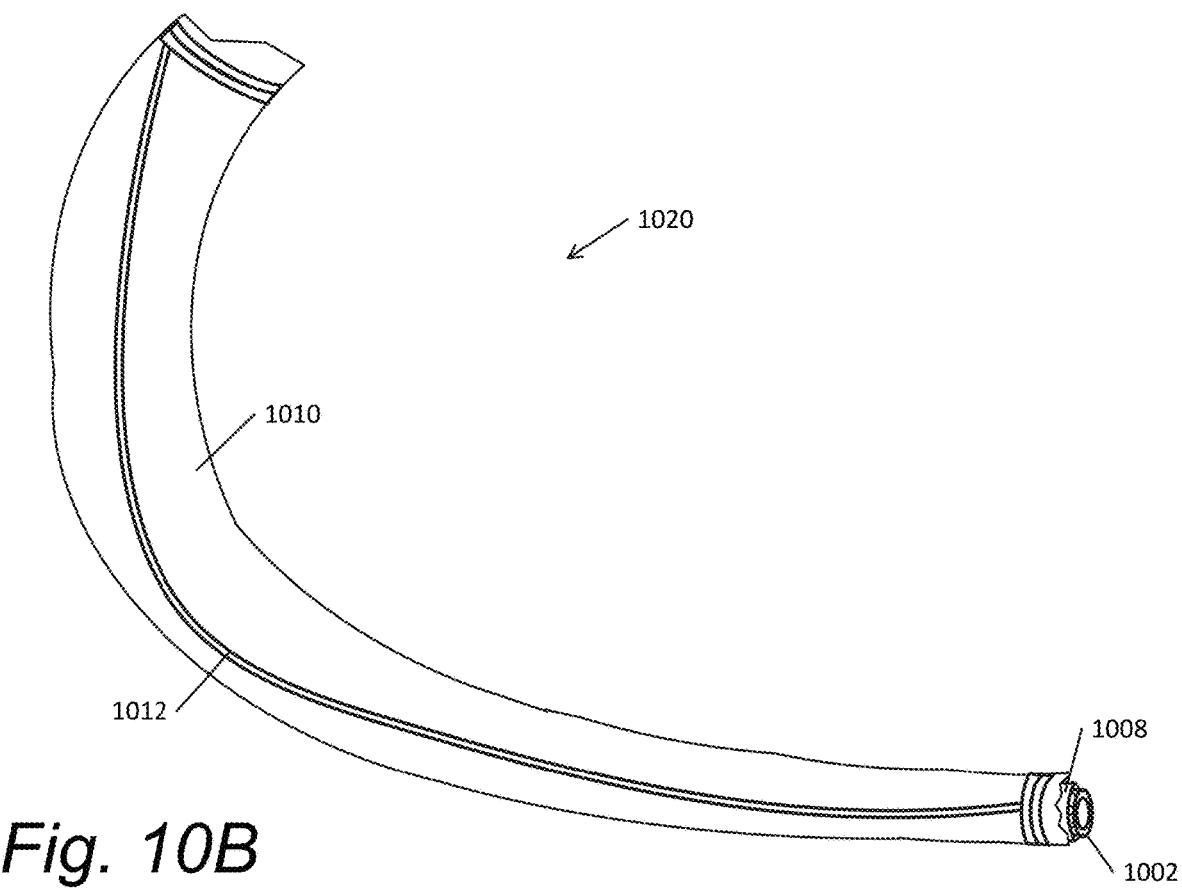
FIG. 10B is a diagram illustrating an embodiment of a spermatic cord module for a groin hernia anatomy training model.

A perspective view of a spermatic cord module 1020 including the layers of spermatic cord 1000 is shown in FIG. 10B. In the embodiment of FIG. 10B, simulated inner and outer sheaths 1008 and 1010 are extended to nearly the end of simulated vas deferens duct 1002. Spermatic cord module 1020 also includes a simulated nerve 1012 disposed along the outer surface of simulated outer sheath 1010. In an embodiment, simulated nerve 1012 represents a patient's ilioinguinal nerve. In an embodiment, simulated nerve 1012 is formed from an elongated structure or material, having a generally filamentary shape. Such materials may include, without limitation, threads, strings, yarns, plastic cording, wires, flexible tubing, or combinations of these. In an embodiment, simulated nerve 1012 is attached to the outer surface of simulated outer sheath 1010. In a further embodiment, simulated nerve 1012 is attached to the outer surface of simulated outer sheath 1010 at locations near the ends of spermatic cord module 1020, but not attached along its entire length. Simulated nerve 1012 may be attached to the outer surface of simulated outer sheath 1010 by any suitable means, including tying, sewing, stapling, nonpermanent fasteners such as those described herein, and/or adhesives.

Figure 10C:
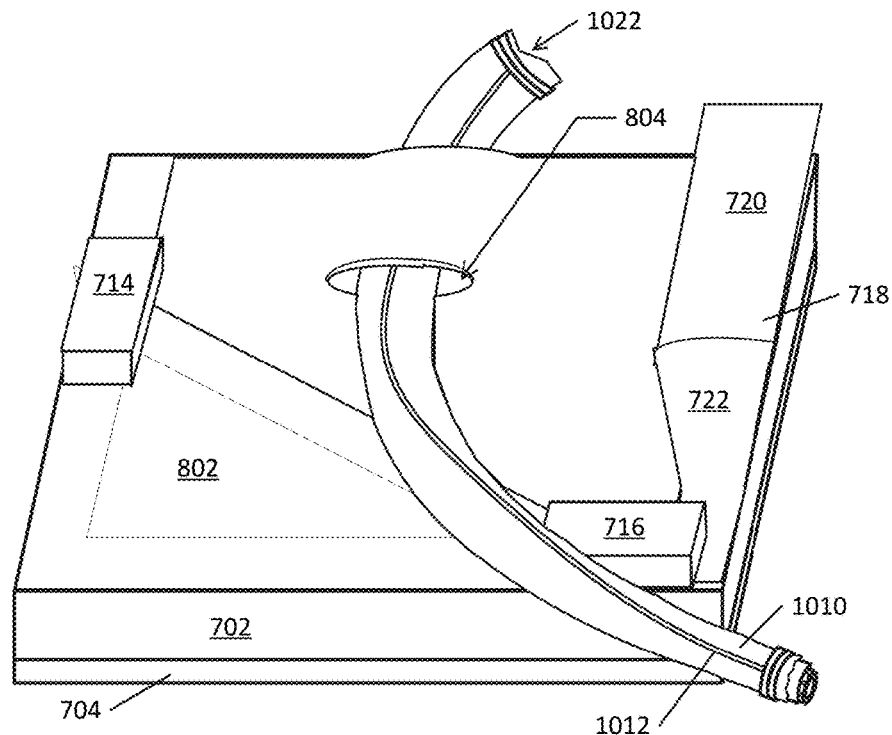
FIG. 10C is a diagram illustrating combination of an embodiment of a spermatic cord module with embodiments of a base unit and lower abdominal wall module layer.
Figure 10D:
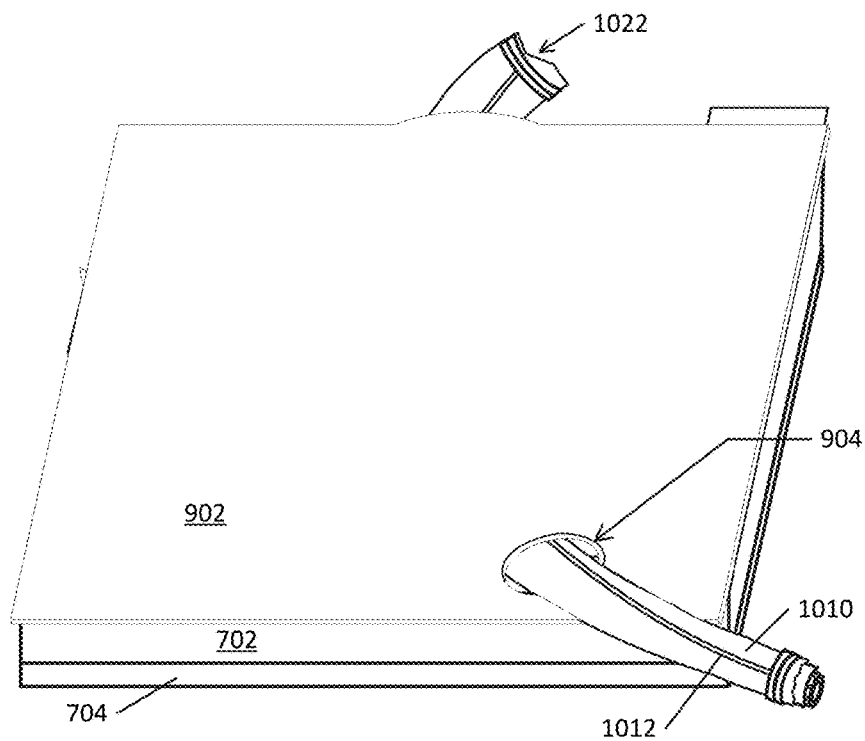
FIG. 10D is a diagram illustrating combination of an embodiment of a spermatic cord module with embodiments of a base unit and abdominal wall module.

The simplified perspective views of FIGS. 10C and 10D illustrate incorporation of spermatic cord module 1020 into the lower and upper layers, respectively, of an abdominal wall module of an embodiment of a groin hernia training model. In the embodiment of FIGS. 10C and 10D, spermatic cord module 1020 passes through opening 804 of lower layer 802 and through opening 904 of upper layer 902. As noted above in the discussion of FIG. 9C, this arrangement simulates passage of a patient's spermatic cord through the inguinal canal between the internal and external inguinal rings. In an embodiment, one or both of openings 804 and 904 is reinforced using an annular structure attached around the inner surface of the opening. In a further embodiment, such an annular structure is somewhat flexible but provides some degree of additional rigidity to the reinforced opening. In an embodiment, such a reinforcing structure simulates layers of muscle and/or fascia surrounding a patient's external and/or internal inguinal ring. An annular reinforcing structure may be formed from any suitable material, including but not limited to cloth, flexible plastic, flexible foam, or cardboard. As an example, an annular reinforcing structure may be formed using a short length of tubing, or from an appropriately-sized elastic band. In some embodiments, outer sheath 1010 of spermatic cord module 1020 is removably attached, at one or more points, to one or both of layers 802 and 902.

In the embodiment of FIGS. 10C and 10D, the upper part of spermatic cord module 1020 extends a short distance beyond the respective outer edges of layers 802 and 902. Opening 1022 into spermatic cord module 1020 allows insertion of a simulated hernia into the spermatic cord module, as discussed further below. In other embodiments, spermatic cord module 1020 is dimensioned such that it does not extend beyond the outer edges of layers 802 and 902. In an embodiment, outer sheath 1010 begins at or just above opening 804 of layer 802.

In the embodiment of FIG. 10D, the lower part of spermatic cord module 1020 extends a short distance beyond opening 904 of layer 902. In other embodiments, a simulated testicle and/or simulated scrotum can be attached to the lower end of spermatic cord module 1020. In an embodiment, outer sheath 1010 is formed from a material having sufficient diameter and/or elasticity to accommodate extension of a simulated hernia through the full length of outer sheath 1010 and into a simulated scrotum attached to the lower end of spermatic cord module 1020. In a further embodiment, inner sheath 1008 or any other sheath included in spermatic cord module 1020 is also formed from a material having sufficient diameter and/or elasticity to accommodate a simulated hernia.

Variations and modifications of spermatic cord module 1020 will be apparent to those skilled in the arts of anatomy and surgery in view of this disclosure. For example, dimensions of the components and structures shown may vary depending on the size and condition of a patient being simulated. Structures and/or depictions representing additional layers, nerves, arteries and other structures may be included in other embodiments depending on the details of the anatomy being simulated and/or the level of anatomical detail required.

Hernia Module

In the case of a typical indirect, or oblique, inguinal hernia, a section of intestine passes into the inguinal canal through the internal ring, and is within one or more of the sheaths surrounding the spermatic cord. In an embodiment of the groin hernia training model, a hernia module allows a simulated hernia to be passed into the spermatic cord module through opening 1022 shown in FIGS. 10C and 10D. The simulated hernia can be positioned at various points along the spermatic cord module to simulate various specific types of hernia. In an embodiment, the simulated hernia is extended through the entire length of the spermatic cord module and into an attached simulated scrotum.

Figure 11A:
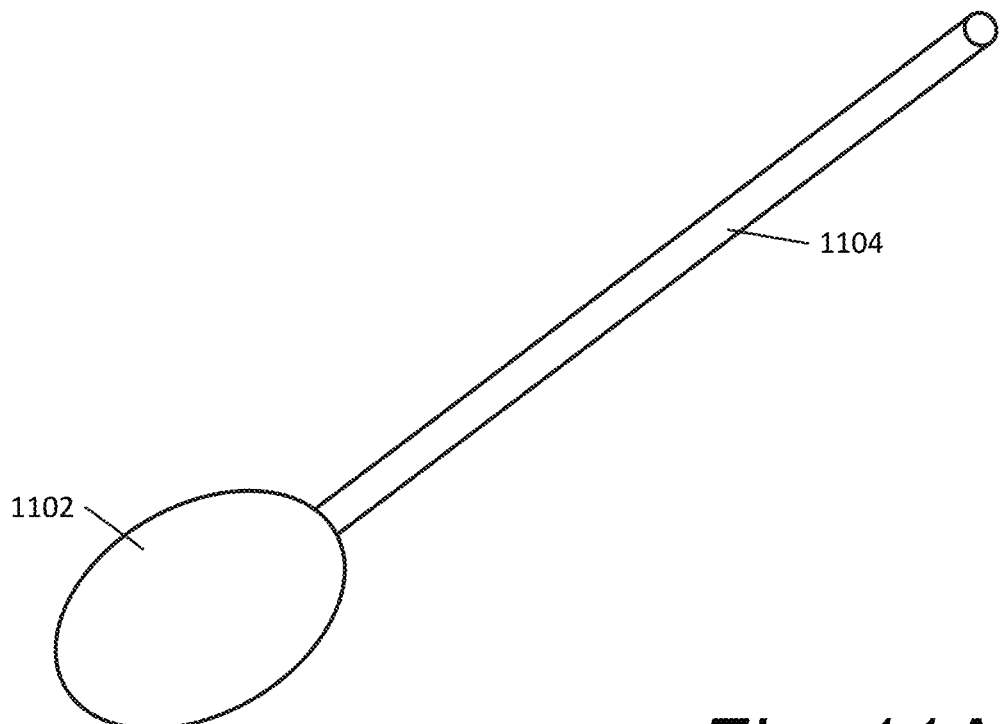
FIG. 11A is diagram illustrating certain aspects of an embodiment of a hernia module for a groin hernia anatomy training model.
Figure 11B:
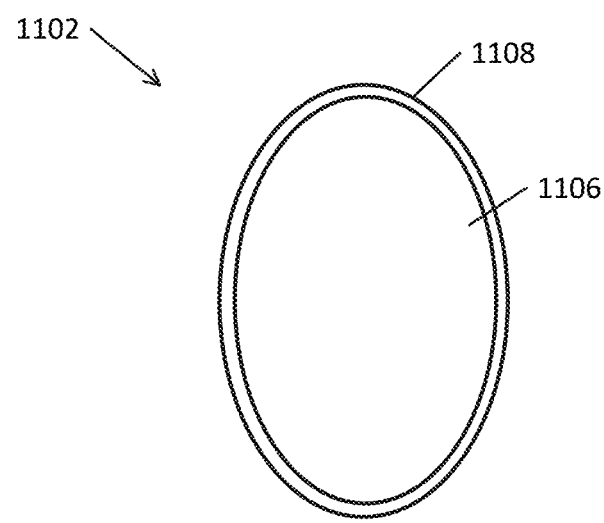
FIG. 11B is a cross-sectional diagram illustrating certain aspects of an embodiment of a hernia model for a groin hernia anatomy training model.

A simplified perspective view of an example of a hernia module is shown in FIG. 11A. In the embodiment of FIG. 11A, hernia model 1102 is attached to handle/extender 1104. In an embodiment, hernia model 1102 is similar to hernia model 206 described above in connection with the ventral hernia training model. As shown in the cross-sectional view of FIG. 11B, hernia model 1102 in such an embodiment includes simulated hernia contents 1106 and simulated hernia sac 1108. In an embodiment, hernia contents 1106 represents a portion of intestine, or bowel, and hernia sac 1108 represents peritoneum. Hernia model 1102 may be formed from any suitable materials, including without limitation those described above in connection with hernia model 206. In an embodiment, handle/extender 1104 is used to insert and position hernia model 1102 within or through spermatic cord module 1020. Handle/extender 1104 can be formed from any material having sufficient rigidity for this purpose, including but not limited to plastic, wood, metal or cardboard. In some embodiments, handle/extender 1104 is substantially permanently attached to hernia model 1102, or at least to hernia contents 1106. In other embodiments, handle/extender 1104 is removably attached to hernia model 1102, so that the handle can be used to insert and position the hernia model, then removed (leaving the hernia model in place), and then reattached to the hernia model in order to retract or remove it. Such a removable attachment mechanism may include, without limitation, a screw mechanism or a pin-and-slot mechanism. In one low-cost embodiment of a hernia module, a large cotton swab is used to implement simulated hernia contents 1106 attached to a handle 1104. In a further embodiment, a latex balloon is disposed over the cotton end of the swab to implement simulated hernia sac 1108.

Figure 11C:
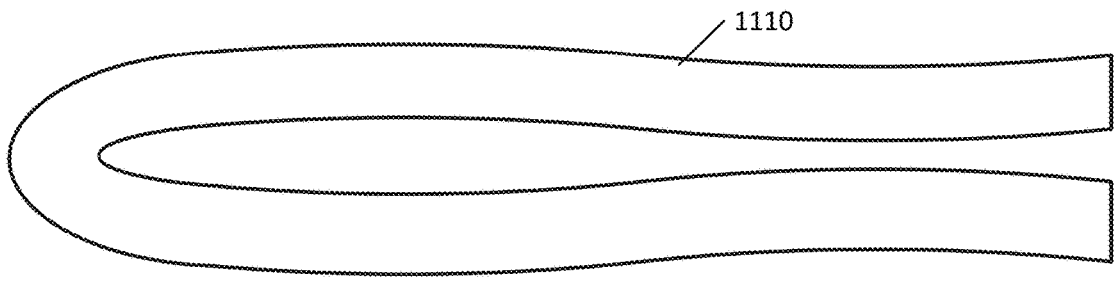
FIG. 11C is a diagram illustrating certain aspects of another embodiment of a hernia model for a groin hernia anatomy training model.
Figure 11D:
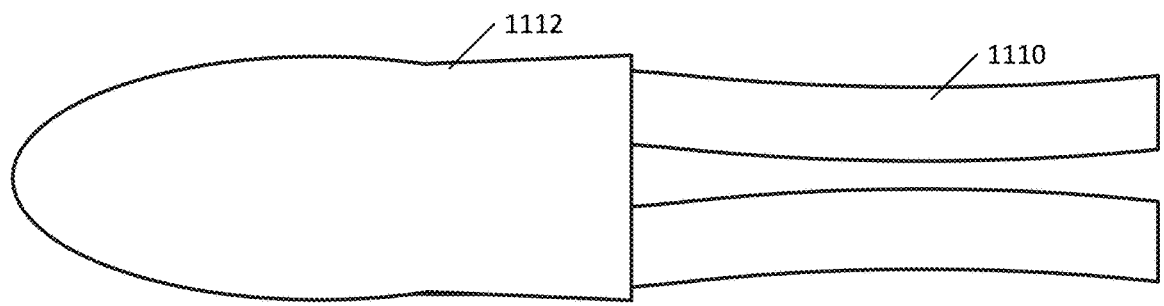
FIG. 11D is a diagram illustrating certain aspects of a further embodiment of a hernia model for a groin hernia anatomy training model.

Simplified top views of another example of a hernia module are shown in FIGS. 11C and 11D. In the embodiment of FIG. 11C, simulated hernia contents 1110 is an elongated structure with a bend at the left side. In an embodiment, the bent end of the structure simulates the end of a fold of intestine forming a hernia. The shape of a structure such as simulated hernia contents 1110 may allow it to be inserted and positioned within a groin hernia training model without any need for an additional handle structure. In an embodiment, contents 1110 is formed from one or more materials having a degree of compressibility, which may provide a more realistic "feel" during a simulated procedure. Alternatively or in addition, contents 1110 is in some embodiments formed from one or more materials having sufficient rigidity to allow the hernia model to be inserted, positioned and retracted by holding the end of the structure opposite the bend. In some embodiments the shape of contents 1110 is fixed, while in other embodiments a flexible structure is used that can be bent or shaped into different configurations. Examples of materials that can be used for contents 1110 include, without limitation, coated or insulated wires or tubes, foam or sponge structures, filled structures such as air-filled balloons, fluid or gel-filled structures and bead-filled structures (such as "bean bag" structures). FIG. 11D shows a top view of hernia contents 1110 inserted into a simulated hernia sac 1112. Like other simulated hernia sacs described herein, simulated hernia sac 1112 may be formed from a thin, flexible material such as plastic film or fabric, including without limitation plastic bags, balloons, heat shrink tubing and other similar materials.

Rather than passing through the interior inguinal ring along with the spermatic cord, direct inguinal hernias and femoral hernias pass through other openings in the abdominal wall. In some embodiments, hernia modules similar to those shown in FIGS. 11A through 11D are used for simulation of direct inguinal or femoral hernias with the groin hernia training model, as well as for simulation of indirect inguinal hernias. In other embodiments, a hernia module more similar to that described above for the ventral hernia training model may be used for simulation of direct inguinal or femoral hernias. In such an embodiment, for example, a container similar to container 202 of FIG. 2A may be positioned within cavity 706 of FIG. 7B, underlying layer 802. Alternatively, a container such as container 202 may be in some embodiments replaced with a pouch that can be removably attached to the underside of layer 802.

Cutaneous Module

In an embodiment, a cutaneous module for a groin hernia training system is similar to the cutaneous module described above for a ventral hernia training system. In such an embodiment, the cutaneous module may include two component layers: a skin simulation layer and an underlying fat simulation layer. These layers are similar in composition to layers 502 and 504 of cutaneous module 500 discussed above in connection with FIGS. 5A through 5C.

Figure 12A:
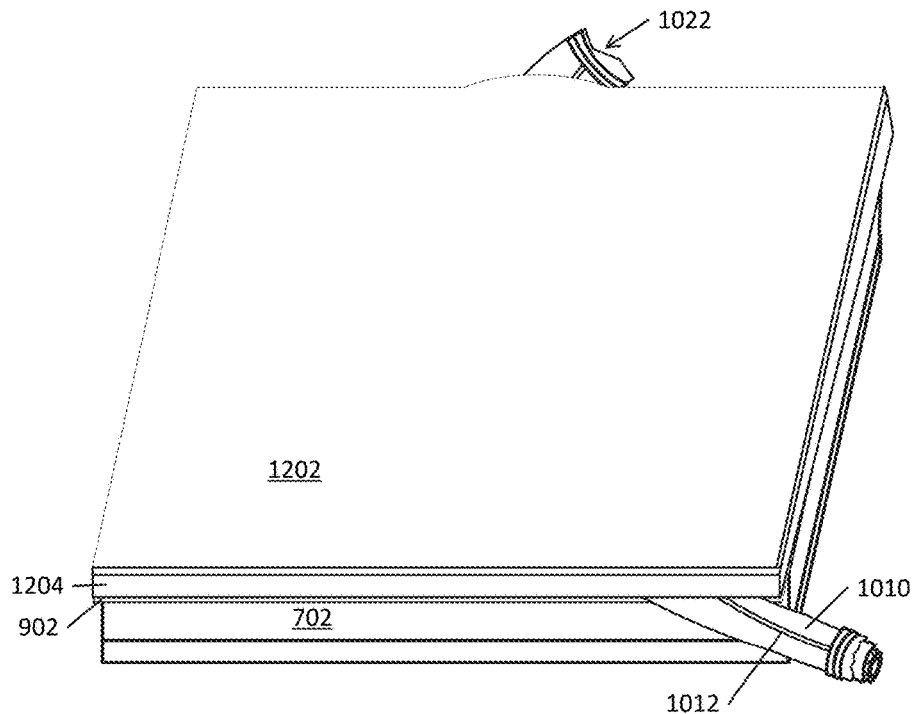
FIG. 12A is a diagram illustrating a combination of an embodiment of a cutaneous module with embodiments of a base unit, abdominal wall module and spermatic cord module.

A simplified perspective view of a cutaneous module overlying the base unit, abdominal wall module and spermatic cord module of FIG. 10D is shown in FIG. 12A. The cutaneous module of FIG. 12A includes a skin simulation layer 1202 and a fat simulation layer 1204. Layers 1202 and 1204 have characteristics and possible variations similar to those described above for layers 502 and 504 shown in FIG. 5C. In an embodiment, fascia such as Campas fascia and Scarpas fascia are represented by layer 1204, in combination with adjacent subcutaneous fat layers. Layers 1202 and 1204 are connected to each other and to an upper surface of the underlying abdominal wall module in similar ways as those described above for cutaneous module 500, including the possible use of spacer elements in some embodiments. The combination of modules in the embodiment of FIG. 12A may be used in combination with a hernia module embodiment as a groin hernia training model.

Figure 12B:
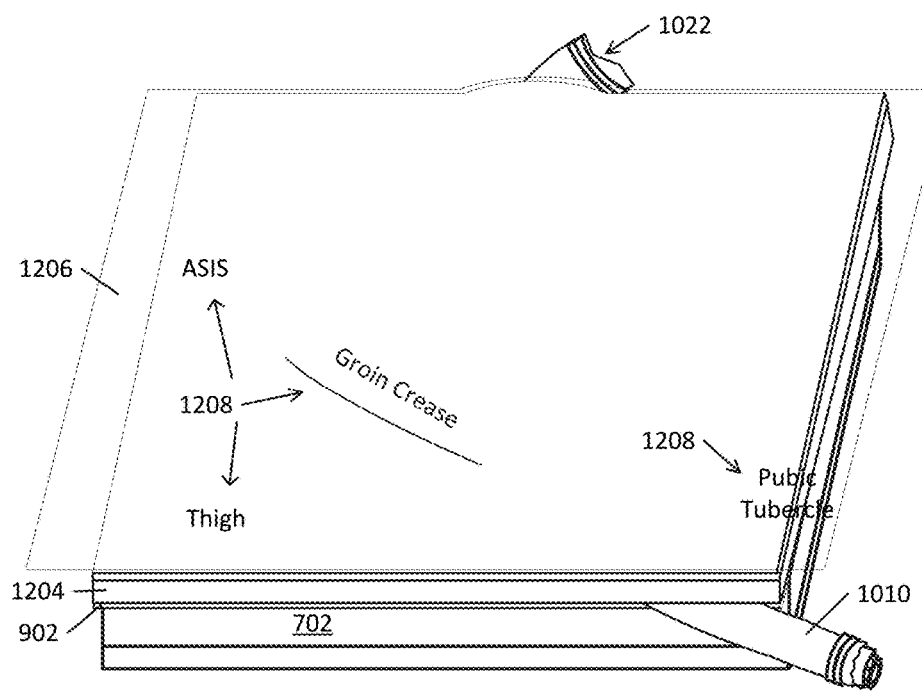
FIG. 12B is a diagram illustrating an embodiment of a groin hernia anatomy training model comprising an additional transparent overlay.

FIG. 12B shows a simplified perspective view of the groin hernia training model of FIG. 12A having an additional transparent overlay 1206. In the embodiment of FIG. 12B, overlay 1206 includes various notations 1208 illustrating patient landmarks. An overlay such as overlay 1206 may be used as a training aid in, for example, allowing a student to first identify patient landmarks without the aid of overlay 1206, and then use overlay 1206 to check against. In an embodiment, overlay 1206 is made from a fluid-resistant material. In such an embodiment, overlay 1206 may be used for protection of underlying parts of the groin hernia training model during simulation of pre-operation sterilization procedures.

In an embodiment, a cutaneous module as described herein is supplied as a component of a groin hernia training model. The cutaneous module can also be supplied separately as a replacement part. In some embodiments, individual layers of a cutaneous module may be supplied as replacement parts. A cutaneous module as described herein may also be used independently from a hernia training model, for example in a cutting or suture trainer. In an embodiment, the uppermost skin simulation layer may be extended or wrapped around the sides of the cutaneous module and attached to the lower surface of the lowest layer of the module. For the cutaneous module, as for other modules and components described herein, any or all of the component layers are in some embodiments formed from liquid-resistant materials.

Use of Groin Hernia Training Model

Embodiments of the groin hernia training model disclosed herein may be used for various purposes, including but not limited to anatomical training and testing, explanation of surgical procedures to patients, and simulation/training for various hernia surgery procedures. In an embodiment, use of a groin hernia training model begins with a stack of elements and modules similar to that illustrated by FIG. 12A. Use may begin with appreciating (in the sense of recognizing or discerning) any external landmarks and orientation of the patient, which may be provided by tactile exploration of the top skin layer and confirmed by a clear plastic overlay with orientations/landmarks explicitly marked. An example of such an overlay is illustrated in FIG. 12B. Pre-operative preparation may be executed as well. The skin and subsequent layers may be intact and a hernia may or may not be appreciated or discerned from the top skin layer depending on the hernia size and type and the body mass index of the patient. In a further embodiment, with reference to the structure of FIG. 12A, having underlying layers and structures also shown in FIGS. 8A through 10D, a model hernia such as those shown in FIGS. 2A and 2B or in FIGS. 11A through 11D is extended at least partially through an opening in lower layer 802 of abdominal wall module 910, as part of the assembly of the training model. The location of the model hernia and of the opening depend on the type of groin hernia being modeled. In the case of an indirect inguinal hernia, for example, a hernia model similar to those in FIGS. 11A through 11D may be extended through opening 804 in lower layer 802 by inserting the hernia model through opening 1022 of spermatic cord module 1020 and pushing it along the length of the spermatic cord module within one or more of the sheath layers of the module. In the case of a direct inguinal hernia or femoral hernia, an additional opening in lower layer 802 may be formed, and a hernia model extended at least partway through the opening from below layer 802.

Continuing with reference to the layers designated in FIG. 12A, the top of the training model presents the substantially smooth surface of upper skin simulation layer 1202. In an embodiment, a palpable "bump" is present at the upper surface as a result of the presence of some or all of a hernia model above lower layer 802 of the underlying abdominal wall module 910. In such an embodiment, use of the training model may include practice in identifying or diagnosing a hernia through palpation of the upper surface of the training model. In some embodiments, a visible feature such as a navel or a scar may be drawn onto the skin simulation layer, or onto a transparent overlay employed for this purpose. Such visual features may assist with practice in diagnosis or in orientation of the training model area with respect to a simulated patient's body.

Use of the hernia training model may also include practice of preoperational procedures such as sterilization techniques (using, for example, BETADINE® or another antiseptic solution), local numbing techniques (for example, using an injection) or draping techniques. As noted above, in some embodiments the skin simulation layer is formed from a liquid-resistant material to prevent damage from practicing with antiseptic solutions or other liquids. In some embodiments, a liquid-resistant layer can be temporarily interposed beneath the skin simulation layer to protect underlying layers from, for example, injected liquids. In an embodiment, the upper surface area of the hernia training model corresponds to the area of a patient's skin exposed by a preoperative draping procedure.

After any preoperational procedures, a simulated hernia repair procedure begins with cutting through the skin simulation layer using an appropriate surgical instrument. Appropriate surgical instruments and techniques will be apparent to those of ordinary skill in the art of hernia repair surgery; it is anticipated that the hernia training model described herein is used by surgical trainees familiar with the procedures being practiced, or at least under the supervision of skilled practitioners. Using the training model embodiment of FIG. 12A, the cut through skin simulation layer 1202 exposes underlying fat simulation layer 1204. Layer 1204 is then cut through or otherwise separated using appropriate instruments, including but not limited to cauterization instruments. In an embodiment, cut or separated edges of layers 1202 and 1204 are pulled back and held using clamps or other suitable instruments.

Formation of an opening in layer 1204 exposes the underlying abdominal wall module. In an embodiment, an opening is formed in upper layer 904 of the abdominal wall module to uncover the hernia model. In the case of a simulated repair of an indirect inguinal hernia, one or more sheath layers of the spermatic cord module are also cut through in order to access the hernia model. Additional separation and retraction, possibly involving additional cutting, of the layers of the abdominal wall module and/or spermatic cord module is performed as needed to obtain sufficient access to the hernia model.

Specific hernia repair procedures may vary based on considerations such as the type and severity of the hernia, other patient indications or contraindications, and local practice. As a general matter, the hernia is typically "reduced" by pushing it back below the abdominal wall. In some embodiments, the hernia is reduced in size as well. Hernia coverings may be cut away in some embodiments. In some embodiments, a portion of the hernia contents may be removed as well. In some cases, hernia repair includes using a piece of a mesh material to help repair or strengthen the abdominal wall after the hernia is reduced. The simulated repair procedure may therefore include placement of a piece of mesh within or alongside the abdominal wall module so that the defect (opening) in an abdominal wall fascia is covered by the mesh. In an embodiment, the specific layers the mesh is inserted alongside depends on the specific technique being employed, or may be a matter of practitioner judgement depending on conditions encountered. In an embodiment, the procedure being simulated includes suturing an inserted mesh piece into place, and suturing of the mesh to the desired layer(s) of the abdominal wall module is performed.

After the hernia repair portion of a simulated procedure is performed, the separate layers of the groin hernia training model are closed and sutured pursuant to the requirements of the procedure being simulated. In an embodiment, the cutaneous module and upper layer of the abdominal wall module are removed from the hernia training model after the simulated hernia repair procedure is completed. The removed cutaneous module and upper layer can be replaced with a fresh (uncut) cutaneous module and upper layer of the abdominal wall module for practicing a new procedure. In addition to replacing the cutaneous module and upper abdominal wall module layer, performing a new procedure using the same hernia training model would in some embodiments require removing any mesh added to the abdominal wall module, and resetting the hernia model into its extended position through an opening in the abdominal wall module. Other cut-into portions of the hernia model, such as, for example, sheaths of the simulated spermatic cord module, would be replaced as well in some embodiments. It is believed that the modular nature of the hernia training model allows such consumable components to be replaced efficiently and economically.

In some embodiments, two or more hernia training models as described herein may be used in conjunction with one another. A system for training may include these two or more models. For example, a groin hernia training model configured to represent the right side of a patient may be arranged next to a groin hernia training model configured to represent the left side of a patient. As another example, in an embodiment one groin hernia training model is configured to simulate primarily the inguinal region and associated hernias, while another groin hernia training model is configured to simulate primarily the femoral region and associated hernias. In such an embodiment, the hernia training models may be configured to be arranged next to one another such that inguinal and femoral regions of a single patient may be simulated. In yet another embodiment, a groin hernia training model may be arranged next to a ventral hernia training model such that abdominal and groin regions of a single patient may be simulated. In an embodiment, hernia training models as disclosed herein are configured to lay next to one another such that realistic anatomical simulation of larger areas of a patient can be achieved. In a further embodiment, hernia training models as disclosed herein are configured to be connected to one another when arranged laterally adjacent.

The description provided herein is meant to be illustrative of the principles and embodiments of the present invention. Numerous variations and modifications will become apparent to those skilled in the art once the above disclosure is fully appreciated. It is intended that any claims be interpreted to embrace all such variations and modifications.

As an example of such variations, multiple manufacturing variations will become apparent to one of ordinary skill in view of this disclosure. Components described separately may in some embodiments be formed into a single integrated structure. Multiple manufacturing techniques may be employed in creating the various components and assemblies described herein, including without limitation 3-D printing and injection molding. Components and structures described herein may be made using various approaches, such as low-cost approaches utilizing existing components, or high-realism approaches utilizing custom-manufactured components. In some embodiments, highly realistic components may include synthetic skin. In further embodiments, synthetic skin having a simulated bleeding capability may be used.

What is claimed is:

1. A system for anatomical training, comprising:
    a portable base unit;
    a flexible simulated abdominal wall module adapted for removable attachment over an upper surface of the base unit;
    a flexible simulated cutaneous module adapted for removable attachment over the simulated abdominal wall module; and
    a simulated hernia module adapted for placement between the base unit and the simulated abdominal wall module, wherein
        the simulated abdominal wall module and simulated cutaneous module are each adapted to be cut or sutured using surgical instruments and supplies, and
        the simulated hernia module is adapted for reversible extension of a simulated hernia through an opening in the simulated abdominal wall module.

2. The system of claim 1, wherein the cutaneous module comprises a skin simulation layer and a fat simulation layer.

3. The system of claim 1, wherein
    the base unit comprises a cavity, and
    an opening of the cavity is within the upper surface of the base unit.

4. The system of claim 3, further comprising a simulated inguinal ligament attached to the upper surface of the base unit and extending across the opening of the cavity.

5. The system of claim 4, wherein the simulated abdominal wall module comprises
    a lower layer adapted to underlie the simulated inguinal ligament when attached to the base unit, and
    an upper layer adapted to overlie the simulated inguinal ligament and the lower layer when attached to the base unit.

6. The system of claim 5, further comprising a simulated spermatic cord module, wherein
    the spermatic cord module comprises a simulated spermatic cord and a sheath surrounding an outer sidewall of the simulated spermatic cord;
    the sheath is adapted to be cut or sutured using surgical instruments and supplies; and
    the spermatic cord module is adapted to extend through a first opening in the lower layer of the simulated abdominal wall module, overlie a portion of the simulated inguinal ligament, and extend through a second opening in the upper layer of the simulated abdominal wall module.

7. The system of claim 1, wherein the abdominal wall module comprises a simulated muscle layer and a simulated fascia layer.

8. The system of claim 1, further comprising:
    a second portable base unit;
    a second flexible simulated abdominal wall module adapted for removable attachment an upper surface of the second base unit;
    a second flexible simulated cutaneous module adapted for removable attachment over the second simulated abdominal wall module; and
    a second simulated hernia module adapted for placement between the second base unit and the second simulated abdominal wall module, wherein
        the second simulated abdominal wall module and second simulated cutaneous module are each adapted to be cut or sutured using surgical instruments and supplies,
        the second simulated hernia module is adapted for reversible extension of a second simulated hernia through an opening in the second simulated abdominal wall module, and
        the opening in the second simulated abdominal wall module is configured to represent a different anatomical defect location than that represented by the opening in the simulated abdominal wall module.

9. The system of claim 8, wherein the base unit and second base unit are configured to be arranged together upon a horizontal surface such that two different hernia locations in a single patient can be simulated.

10. The system of claim 9, wherein the base unit and second base unit are configured to be removably connected to one another while arranged together upon a horizontal surface.

11. A method of assembling a system for anatomical training, the method comprising:
    attaching a flexible simulated abdominal wall module to a portable base unit, wherein the simulated abdominal wall module overlies an upper surface of the base unit when attached;
    attaching a flexible simulated cutaneous module to one or more of the simulated abdominal wall module or the portable base unit, wherein the simulated cutaneous module overlies an upper surface of the simulated abdominal wall module when attached; and
    positioning a simulated hernia to be extended through an opening in the simulated abdominal wall module.

12. The method of claim 11, further comprising creating the opening in the simulated abdominal wall module.

13. The method of claim 11, wherein positioning the simulated hernia comprises:
    placing the simulated hernia into a cavity within the upper surface of the base unit; and
    pulling a portion of the simulated hernia through the opening in the simulated abdominal wall module.

14. The method of claim 11, wherein:
    the base unit comprises a cavity within its upper surface and a simulated inguinal ligament attached to the upper surface and extending across an opening of the cavity; and
    attaching the simulated abdominal wall module comprises positioning a lower layer of the simulated abdominal wall module below the simulated inguinal ligament, and positioning an upper layer of the simulated abdominal wall module above the simulated inguinal ligament.

15. The method of claim 14, further comprising:

inserting an end of a simulated spermatic cord module through a first opening in the lower layer of the simulated abdominal wall module; and inserting the end of the simulated spermatic cord module through a second opening in the upper layer of the simulated abdominal wall module.

16. A method of using a system for anatomical training, the method comprising:

forming an opening in a flexible simulated cutaneous module, wherein the simulated cutaneous module is attached to one or both of an underlying simulated abdominal wall module and an underlying portable base unit;

locating a simulated hernia extending through an opening in the simulated abdominal wall module;

performing a repair of the simulated hernia; and closing the opening in the simulated cutaneous module.

17. The method of claim 16, wherein locating the simulated hernia comprises:

forming an opening in an upper layer of the simulated abdominal wall module; and locating the simulated hernia extending through an opening in a lower layer of the simulated abdominal wall module.

18. The method of claim 17, wherein locating the simulated hernia further comprises locating the simulated hernia within a portion of a simulated spermatic cord module disposed between the upper layer and lower layer of the simulated abdominal wall module.

19. The method of claim 18, wherein locating the simulated hernia further comprises forming an opening in a sheath layer of the portion of the simulated spermatic cord module.

20. The method of claim 16, wherein performing the repair comprises pushing the simulated hernia back through the opening in the simulated abdominal wall module.

21. The method of claim 20, wherein pushing the simulated hernia back through the opening comprises pushing the simulated hernia back through the simulated spermatic cord.

22. The method of claim 20, wherein performing the repair further comprises covering at least a portion of the opening in the simulated abdominal wall module with a piece of surgical mesh.

23. The method of claim 16, further comprising, prior to forming the opening, applying a sterilization solution to an upper surface of the simulated cutaneous module.

* * * * *